US012575924B2

(12) United States Patent
Sarver et al.

(10) Patent No.: US 12,575,924 B2
(45) Date of Patent: Mar. 17, 2026

(54) HIGH DEFINITION AND EXTENDED DEPTH OF FIELD INTRAOCULAR LENS

(71) Applicant: Z Optics, Inc., Cookeville, TN (US)

(72) Inventors: Edwin J. Sarver, Cookeville, TN (US); James J. Simms, Medford, NJ (US)

(73) Assignee: Z Optics, Inc., Cookeville, TN (US)

( * ) Notice: Subject to any disclaimer, the term of this patent is extended or adjusted under 35 U.S.C. 154(b) by 882 days.

(21) Appl. No.: 17/618,616

(22) PCT Filed: Jun. 10, 2020

(86) PCT No.: PCT/US2020/037014
§ 371 (c)(1),
(2) Date: Dec. 13, 2021

(87) PCT Pub. No.: WO2020/252034
PCT Pub. Date: Dec. 17, 2020

(65) Prior Publication Data
US 2022/0249223 A1     Aug. 11, 2022

Related U.S. Application Data

(60) Provisional application No. 62/988,802, filed on Mar. 12, 2020, provisional application No. 62/986,115, (Continued)

(51) Int. Cl.
*A61F 2/16* (2006.01)

(52) U.S. Cl.
CPC .... *A61F 2/1637* (2013.01); *A61F 2002/1681* (2013.01)

(58) Field of Classification Search
CPC ............ A61F 2/1637; A61F 2002/1681; A61F 2250/0026; A61F 2250/0053; A61F 2/1656; A61F 2/1645; G02C 7/02
See application file for complete search history.

(56) References Cited

U.S. PATENT DOCUMENTS

| | | |
|---|---|---|
| 4,976,732 A | 12/1990 | Vorosmarthy |
| 5,121,980 A | 6/1992 | Cohen |

(Continued)

FOREIGN PATENT DOCUMENTS

| | | |
|---|---|---|
| EP | 2030594 A1 | 3/2009 |
| JP | 2003-514614 A | 4/2003 |

(Continued)

OTHER PUBLICATIONS

Nishi, Y. et al. (2015). "Visual Simulation of Retinal Images with Various Designs of Pinhole Contact Lenses." JSM Ophthalmol. 3(1):1025 (5 pages).

(Continued)

*Primary Examiner* — Suzette J Gherbi
(74) *Attorney, Agent, or Firm* — Mintz Levin Cohn Ferris Glovsky and Popeo, P.C.

(57) ABSTRACT

Disclosed are systems, devices, and methods that overcome limitations of IOLs at least by providing a phakic or aphakic IOL that provides correction of defocus and astigmatism, decreases higher-order monochromatic and chromatic aberrations, and provides an extended depth of field to improve vision quality. The IOL includes a virtual aperture integrated into the IOL. The construction and arrangement permit optical rays which intersect the virtual aperture and are widely scattered across the retina, causing the light to be virtually prevented from reaching detectable levels on the retina. The virtual aperture helps remove monochromatic and chromatic aberrations, yielding high-definition retinal images. For a given definition of acceptable vision, the depth of field is increased over a larger diameter optical zone IOL.

17 Claims, 28 Drawing Sheets

Related U.S. Application Data filed on Mar. 6, 2020, provisional application No. 62/861,120, filed on Jun. 13, 2019.

(56) References Cited

U.S. PATENT DOCUMENTS

| | | | |
|---|---|---|---|
| 5,628,794 | A | 5/1997 | Lindstrom |
| 5,662,706 | A | 9/1997 | Legerton et al. |
| 5,693,094 | A | 12/1997 | Young et al. |
| 5,965,330 | A | 10/1999 | Evans et al. |
| 5,980,040 | A | 11/1999 | Xu et al. |
| 6,221,067 | B1 | 4/2001 | Peyman |
| 6,364,483 | B1 | 4/2002 | Grossinger et al. |
| 6,485,516 | B2 | 11/2002 | Boehm |
| 6,874,886 | B2 | 4/2005 | Miller et al. |
| 6,949,093 | B1 | 9/2005 | Peyman |
| 7,287,852 | B2 | 10/2007 | Fiala |
| 7,350,918 | B2 | 4/2008 | Clough et al. |
| 7,491,350 | B2 | 2/2009 | Silvestrini |
| 7,628,810 | B2 | 12/2009 | Christie et al. |
| 7,976,577 | B2 | 7/2011 | Silvestrini |
| 8,079,706 | B2 | 12/2011 | Silvestrini et al. |
| D656,526 | S | 3/2012 | Christie et al. |
| 8,241,354 | B2 | 8/2012 | Hong et al. |
| 8,287,592 | B2 | 10/2012 | Silvestrini |
| 8,343,215 | B2 | 1/2013 | Miller et al. |
| D681,086 | S | 4/2013 | Christie et al. |
| 8,460,374 | B2 | 6/2013 | Christie et al. |
| 8,740,978 | B2 | 6/2014 | Weeber et al. |
| 8,747,466 | B2 | 6/2014 | Weeber et al. |
| 8,752,958 | B2 | 6/2014 | Miller et al. |
| 8,858,624 | B2 | 10/2014 | Christie et al. |
| 8,864,824 | B2 | 10/2014 | Silvestrini et al. |
| 8,974,526 | B2 | 3/2015 | Bogaert |
| 9,005,281 | B2 | 4/2015 | Christie et al. |
| 9,138,142 | B2 | 9/2015 | Christie et al. |
| 9,204,962 | B2 | 12/2015 | Silvestrini |
| 9,427,311 | B2 | 8/2016 | Christie et al. |
| 9,427,922 | B2 | 8/2016 | Reboul et al. |
| 9,492,272 | B2 | 11/2016 | Christie et al. |
| 9,545,303 | B2 | 1/2017 | Vilupuru et al. |
| 9,573,328 | B2 | 2/2017 | Reboul et al. |
| 9,603,704 | B2 | 3/2017 | Silvestrini |
| 9,636,215 | B2 | 5/2017 | Rosen et al. |
| 9,844,919 | B2 | 12/2017 | Reboul et al. |
| 9,848,979 | B2 | 12/2017 | Vilupuru et al. |
| 9,943,403 | B2 | 4/2018 | Webb et al. |
| 10,004,593 | B2 | 6/2018 | Webb et al. |
| 10,183,453 | B2 | 1/2019 | Reboul et al. |
| 10,285,807 | B2 * | 5/2019 | Sarver .................. A61F 2/1637 |
| 10,765,510 | B2 * | 9/2020 | Sarver .................. A61F 2/1637 |
| 2001/0050750 | A1 | 12/2001 | Breger |
| 2003/0144733 | A1 | 7/2003 | Brady et al. |
| 2003/0199976 | A1 | 10/2003 | Portney |
| 2004/0046934 | A1 * | 3/2004 | Sponsel ................. A61B 3/032 |
| | | | 351/200 |
| 2004/0230299 | A1 | 11/2004 | Simpson et al. |
| 2005/0046794 | A1 | 3/2005 | Silvestrini et al. |
| 2005/0068494 | A1 | 3/2005 | Griffin |
| 2005/0125055 | A1 | 6/2005 | Deacon et al. |
| 2006/0113054 | A1 | 6/2006 | Silvestrini |
| 2006/0184243 | A1 | 8/2006 | Yilmaz |
| 2006/0235428 | A1 | 10/2006 | Silvestrini |
| 2006/0265058 | A1 | 11/2006 | Silvestrini |
| 2006/0271184 | A1 | 11/2006 | Silvestrini |
| 2007/0018810 | A1 * | 1/2007 | Smythe ................ A61B 5/0031 |
| | | | 340/539.12 |
| 2007/0198084 | A1 | 8/2007 | Cumming et al. |
| 2008/0269882 | A1 | 10/2008 | Simpson et al. |
| 2008/0269886 | A1 | 10/2008 | Simpson et al. |
| 2008/0269890 | A1 | 10/2008 | Simpson et al. |
| 2008/0269891 | A1 | 10/2008 | Hong et al. |
| 2008/0297720 | A1 | 12/2008 | Ballet et al. |
| 2009/0033863 | A1 | 2/2009 | Blum et al. |
| 2009/0051870 | A1 | 2/2009 | Lindacher et al. |
| 2009/0069817 | A1 | 3/2009 | Peyman |
| 2009/0268155 | A1 | 10/2009 | Weeber |
| 2009/0279189 | A1 | 11/2009 | Getman et al. |
| 2009/0306773 | A1 | 12/2009 | Silversrini et al. |
| 2009/0323020 | A1 | 12/2009 | Zhao et al. |
| 2011/0172675 | A1 | 7/2011 | Danta et al. |
| 2011/0317024 | A1 | 12/2011 | Miyasako |
| 2011/0317124 | A1 | 12/2011 | Weeber et al. |
| 2012/0277857 | A1 | 11/2012 | Purchase et al. |
| 2012/0330415 | A1 | 12/2012 | Callahan et al. |
| 2013/0053953 | A1 | 2/2013 | Silvestrini |
| 2013/0238091 | A1 | 9/2013 | Danta et al. |
| 2013/0289668 | A1 | 10/2013 | Nirenberg et al. |
| 2014/0052245 | A1 | 2/2014 | Zickler et al. |
| 2014/0055744 | A1 | 2/2014 | Wildsmith et al. |
| 2014/0131905 | A1 | 5/2014 | Webb |
| 2014/0172088 | A1 | 6/2014 | Carson et al. |
| 2014/0293426 | A1 | 10/2014 | Dobschal |
| 2014/0303725 | A1 | 10/2014 | Barrett et al. |
| 2014/0327875 | A1 | 11/2014 | Blum et al. |
| 2014/0379078 | A1 | 12/2014 | Trindade |
| 2015/0005877 | A1 | 1/2015 | Wanders |
| 2015/0025627 | A1 | 1/2015 | Christie et al. |
| 2015/0359625 | A1 | 12/2015 | Argal et al. |
| 2015/0366658 | A1 | 12/2015 | Christie et al. |
| 2016/0157997 | A1 | 6/2016 | Gerlach |
| 2016/0193037 | A1 | 7/2016 | Pinto et al. |
| 2016/0302916 | A1 * | 10/2016 | Sarver .................... A61F 2/1637 |
| 2017/0042665 | A1 | 2/2017 | Currie et al. |
| 2017/0143477 | A1 | 5/2017 | Christie et al. |
| 2017/0156850 | A1 | 6/2017 | Silvestrini |
| 2017/0290657 | A1 | 10/2017 | Luque |
| 2018/0110613 | A1 | 4/2018 | Wortz et al. |
| 2018/0125639 | A1 | 5/2018 | Vilupuru et al. |
| 2018/0141942 | A1 * | 5/2018 | McMaster .............. C07J 31/006 |
| 2018/0275427 | A1 | 9/2018 | Lau et al. |
| 2018/0296322 | A1 | 10/2018 | Webb et al. |
| 2018/0338826 | A1 | 11/2018 | Link et al. |
| 2019/0021847 | A1 | 1/2019 | Hong et al. |
| 2019/0076235 | A1 | 3/2019 | Webb et al. |
| 2019/0076242 | A1 | 3/2019 | Pinto |
| 2019/0169187 | A1 * | 6/2019 | McMaster .............. C07J 31/006 |
| 2019/0231518 | A1 * | 8/2019 | Sarver .................... A61F 9/008 |
| 2019/0307556 | A1 | 10/2019 | Sarver et al. |
| 2020/0017494 | A1 * | 1/2020 | McMaster ................. A61P 9/00 |
| 2021/0228337 | A1 | 7/2021 | Sarver et al. |
| 2021/0298893 | A1 | 9/2021 | Sarver et al. |
| 2022/0249223 | A1 * | 8/2022 | Sarver .................. A61F 2/1656 |
| 2023/0010847 | A1 * | 1/2023 | Sarver .................. G02B 3/0056 |

FOREIGN PATENT DOCUMENTS

| | | | |
|---|---|---|---|
| WO | WO-01/15635 | A1 | 3/2001 |
| WO | WO-01/37762 | A1 | 5/2001 |
| WO | WO-2006/054178 | A2 | 5/2006 |
| WO | WO-2008/137425 | A2 | 11/2008 |
| WO | WO-2010/100523 | A1 | 9/2010 |
| WO | WO-2010/102227 | A1 | 9/2010 |
| WO | WO-2014/054946 | A1 | 4/2014 |
| WO | WO-2016/142736 | A1 | 9/2016 |
| WO | WO-2016/167906 | A1 | 10/2016 |
| WO | WO-2018/076057 | A1 | 5/2018 |

OTHER PUBLICATIONS

Smith, George (1991). "Relation between Spherical Refractive Error and Visual Acuity." Optometry Vis. Sci., vol. 68, No. 8, pp. 591-598.

Yaish, S.B. et al. (2010). "Intraocular Omni-focal Lens With Increased Tolerance to Decentration and Astigmatism." J Refract Surg. 26(1):71-76.

* cited by examiner

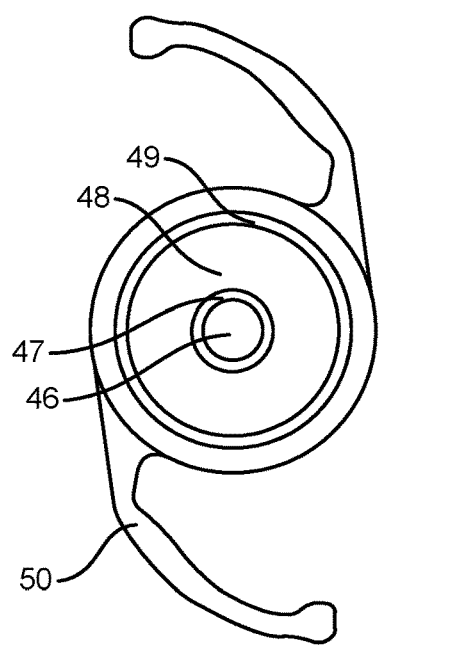
Front View
FIG. 6A
Back view
FIG. 6B
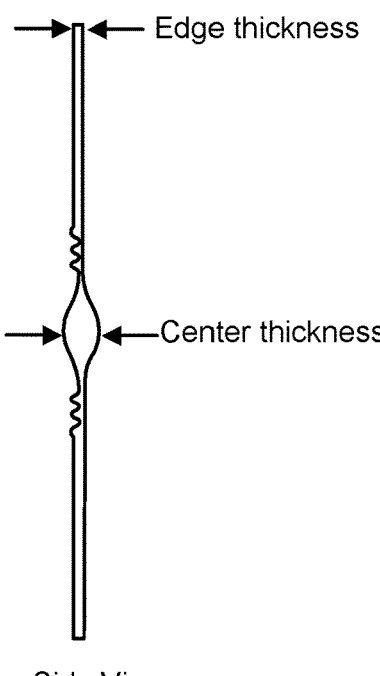
Side View
FIG. 6C Light propagation Light propagation

| Combination | Anterior | Posterior |
|---|---|---|
| 1 | Smooth | Smooth |
| 2 | Smooth | Ripples |
| 3 | Smooth | Micro-Prisms |
| 4 | Ripples | Smooth |
| 5 | Ripples | Ripples |
| 6 | Ripples | Micro-Prisms |
| 7 | Micro-Prisms | Smooth |
| 8 | Micro-Prisms | Ripples |
| 9 | Micro-Prisms | Micro-Prisms |

FIG. 15

HIGH DEFINITION AND EXTENDED DEPTH OF FIELD INTRAOCULAR LENS

CROSS-REFERENCE TO RELATED APPLICATIONS

This application is a U.S. national stage application, filed under 35 U.S.C. § 371, of International Patent Application No. PCT/US2020/037014, filed on Jun. 10, 2020, which claims priority to U.S. Patent Application No. 62/861,120 entitled "HIGH DEFINITION AND EXTENDED DEPTH OF FIELD INTRAOCULAR LENS" filed Jun. 13, 2019, U.S. Patent Application No. 62/986,115 entitled "HIGH DEFINITION AND EXTENDED DEPTH OF FIELD INTRAOCULAR LENS" filed Mar. 6, 2020, U.S. Patent Application No. 62/988,802 entitled "MICRO-PRISM REGION FOR EXTENDED DEPTH OF FOCUS INTRAOCULAR LENS" filed Mar. 12, 2020. The contents of the above referenced applications are incorporated herein by reference in their entirety.

BACKGROUND

The human eye often suffers from aberrations such as defocus and astigmatism that must be corrected to provide acceptable vision to maintain a high quality of life. Correction of these defocus and astigmatism aberrations can be accomplished using a lens. The lens can be located, for example, at a spectacle plane, at the corneal plane (a contact lens or corneal implant), or within the eye as a phakic (crystalline lens intact) or aphakic (crystalline lens removed) intraocular lens (IOL).

In addition to the basic aberrations of defocus and astigmatism, the eye often has higher-order aberrations such as spherical aberration and other aberrations. Chromatic aberrations, which are generally aberrations due to varying focus with wavelength across the visible spectrum, are also present in the eye. These higher-order aberrations and chromatic aberrations negatively affect the quality of a person's vision. The negative effects of the higher-order and chromatic aberrations increase as the pupil size increases. Vision with these aberrations removed is often referred to as high definition (HD) vision.

Presbyopia is the condition where the eye loses its ability to focus on objects at different distances. Aphakic eyes have presbyopia. A standard monofocal IOL implanted in an aphakic eye restores vision at a single focal distance. A variety of devices and procedures are used to provide improved vision over a range of distances, among them, using a monofocal IOL combined with bi-focal or progressive addition spectacles. A monovision IOL system is another option to restore near and distance vision—one eye is set at a different focal length than the fellow eye, thus providing binocular summation of the two focal points and providing blended visions. Monovision is currently the most common method of correcting presbyopia by using IOLs to correct the dominant eye for distance vision and the non-dominant eye for near vision in an attempt to achieve spectacle-free binocular vision from far to near.

Additionally, IOLs can be multifocal, for example, bifocal (having two focal regions—usually far and near) or trifocal (having three focal regions—far, intermediate, and near). Most multifocal IOLs are designed to have one or more focal regions distributed within an addition range. However, using elements with a set of discrete foci is not the only possible strategy of design: the use of elements with extended depth of field (EDOF), that is, elements producing a continuous focal segment spanning the required addition, can also be considered. These methods are not entirely acceptable as stray light from the various focal regions degrade a person's vision.

SUMMARY

Disclosed are systems, devices, and methods that overcome limitations of IOLs at least by providing a phakic or aphakic IOL that provides correction of defocus and astigmatism, decreases higher-order monochromatic and chromatic aberrations, and provides an extended depth of field to improve vision quality. The IOL includes a virtual aperture integrated into the IOL. The construction and arrangement permit optical rays which intersect the virtual aperture and are widely scattered across the retina, causing the light to be virtually prevented from reaching detectable levels on the retina. The virtual aperture helps remove monochromatic and chromatic aberrations, yielding high-definition retinal images. For a given definition of acceptable vision, the depth of field is increased over a larger diameter optical zone IOL.

In one aspect, there is disclosed an intraocular lens for providing an extended depth-of-field, said intraocular lens comprising: an optical zone comprising at least one anterior optical surface and at least one posterior optical surface; a first periphery region peripherally positioned relative to the optical zone, the first periphery region comprising a virtual aperture, the virtual aperture comprising an anterior virtual aperture surface and a posterior virtual aperture surface; and a second periphery region peripherally positioned relative to the first periphery region, the second periphery region comprising a haptic for positioning the intraocular lens within an eye, wherein the haptic comprises an outermost region of the intraocular lens; wherein a first plurality of light rays incident on the anterior optical surface pass through the optical zone to form an image on a retina when the intraocular lens is implanted in an eye; and at least one of: (a) a first surface contour on an anterior surface of the intraocular lens, the first surface contour comprising at least one annular region; and (b) a second surface contour on a posterior surface of the intraocular lens, the second surface contour comprising at least one annular region; wherein a second plurality of light rays incident on the anterior virtual aperture surface are dispersed widely downstream from the intraocular lens towards and across the retina, such that the image comprises the extended depth-of-field and further wherein said virtual aperture reduces monochromatic and chromatic aberrations in the image.

In a related method, an IOL, such as any embodiment of an IOL described herein, is implanted or otherwise coupled to an eye, such as a human eye. The IOL is used to modify or adjust a transmission of lights rays onto a retina of an eye pursuant to the features described herein.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

FIGS. 6A, 6B, and 6C illustrates an overall structure of an example IOL.

FIG. 15 shows a table with a variety of combinations of surface contours between the anterior surface and the posterior surface of the IOL or a portion of the IOL.

DETAILED DESCRIPTION

Before the present subject matter is further described, it is to be understood that this subject matter described herein is not limited to particular embodiments described, as such may of course vary. It is also to be understood that the terminology used herein is for the purpose of describing particular embodiments only, and is not intended to be limiting. Unless defined otherwise, all technical terms used herein have the same meaning as commonly understood by one skilled in the art to which this subject matter belongs.

Disclosed are systems, devices, and methods that overcome limitations of IOLs at least by providing a phakic or aphakic IOL that provides correction of defocus and astigmatism, decreases higher-order monochromatic and chromatic aberrations, and provides an extended depth of field to improve vision quality. The disclosed IOL is sometimes referred to herein as the Z+ optic or Z+ IOL. U.S. Pat. No. 10,285,807 and U.S. patent application Ser. No. 16/380,622 described related systems and methods and are both incorporated herein by reference in their entirety.

Figure 1A:
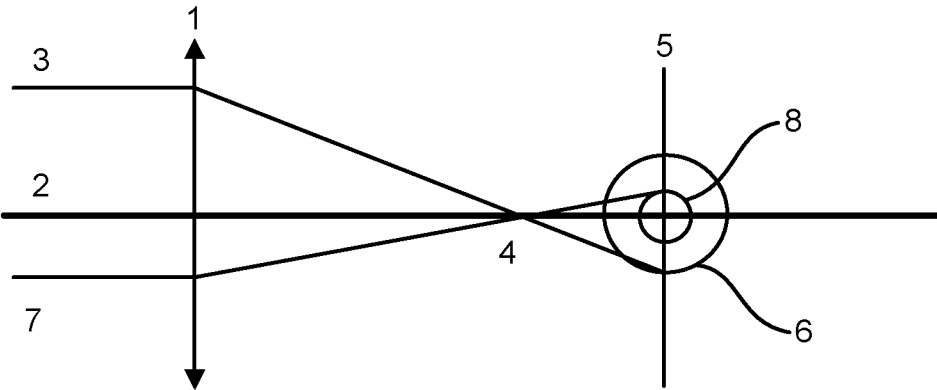
FIGS. 1A and 1B illustrates a basic method of reducing monochromatic aberrations and increasing or extending depth of field using pupil size for a near-sighted eye.

A description of the basic principle used to reduce monochromatic and chromatic aberrations and provide an increased depth of field is now provided. FIG. 1A schematically illustrates a single converging lens 1 centered on an optical axis 2. An incident ray 3 from a distant object is parallel to the optical axis and intersects the focal point 4 (with a suffix b, c, d, or e based on the corresponding figure) of the lens. If the lens power is properly selected, the focal point coincides with the observation plane 5, otherwise there is a mismatch between the lens power and the location of the observation plane such that the focus is in front of or behind the observation plane.

In FIG. 1A, the focal point is in front of the observation plane. If all incident rays are traced with the same ray height as incident ray 3, a blur circle 6 is located on the observation plane 5. The observation plane is oriented orthogonal to the optical axis and so is shown as a vertical line in the figure. The blur circles 6 and 8 are shown in the plane of the figure for visualization convenience, however, the blur circles are actually contained in the observation plane. Other parallel incident rays with ray height less than incident ray 3 fall inside this blur circle 6. One such ray is parallel incident ray 7 which is closer to the optical axis than incident ray 3. Incident ray 7 also intersects the focal point 4 and then the observation plane 5. Tracing all incident rays with ray height equal to incident ray 7 traces out blur circle 8 which has a diameter smaller than that of blur circle 6.

Figure 1B:
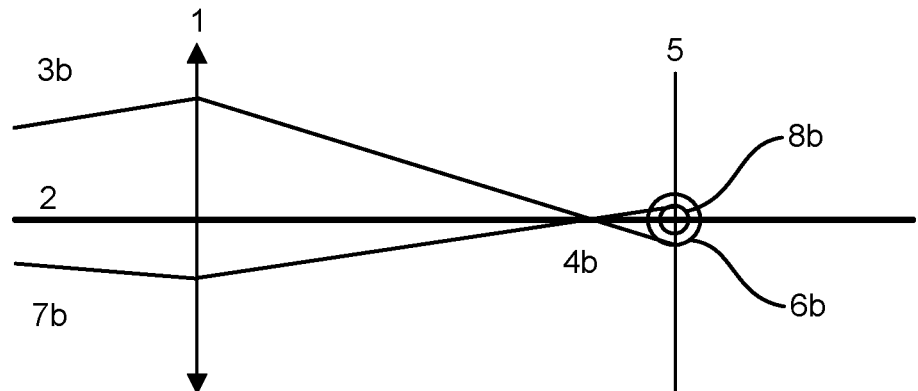

FIG. 1B illustrates the same optical system in FIG. 1A, but now the incident rays are for an object closer to the optical system as indicated by the slopes on incident rays 3b and 7b. The effect is that the focus point 4 (with a suffice a, b, c, r d based on the corresponding figure) for the closer object is now closer to the observation plane and both of the blur circles 6b and 8b are smaller than their counter parts in FIG. 1A, but the principle is the same: rays which intersect the lens 1 closer to the optical axis have smaller blur on the observation plane. To relate this simple optical construction of FIG. 1 to the human eye, the converging lens 1 represents the principal plane of the eye's optics including the cornea and the crystalline lens or an intraocular lens. Observation plane 5 represents the retina. As drawn the focal point 4 is in front of the observation plane (retina), so this figure is for a myopic or near-sighted eye. The size of the blur circles 6 and 8 (or 6b and 8b) represents the amount of defocus on the retina, where a smaller blur circle diameter provides clearer vision than a larger blur circle diameter.

Figure 2A:
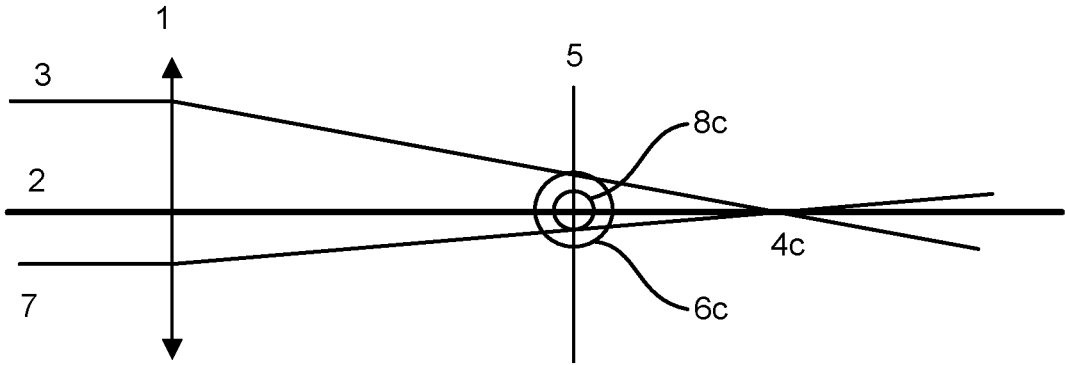
FIGS. 2A and 2B illustrate a basic method of reducing monochromatic aberrations and increasing depth of field using pupil size for a far-sighted eye.
Figure 2B:
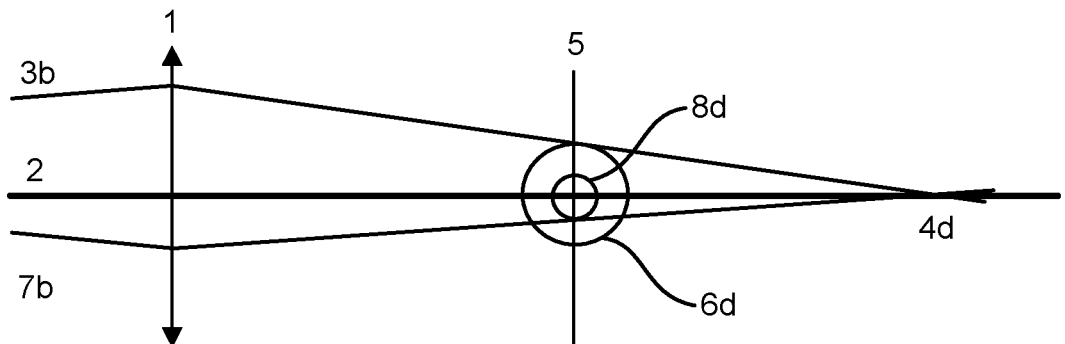

Note that the same relationship regarding incident ray height and blur circle size also holds for hyperopic or far-sighted eyes. This is schematically illustrated in FIGS. 2A and 2B, which show rays corresponding to a far-sighted eye. In FIG. 2A for rays 3 and 7 from a distant object and in FIG. 2B for rays 3b and 7b, smaller ray height leads to a smaller blur circle on the retina (observation plane).

Figure 3A:
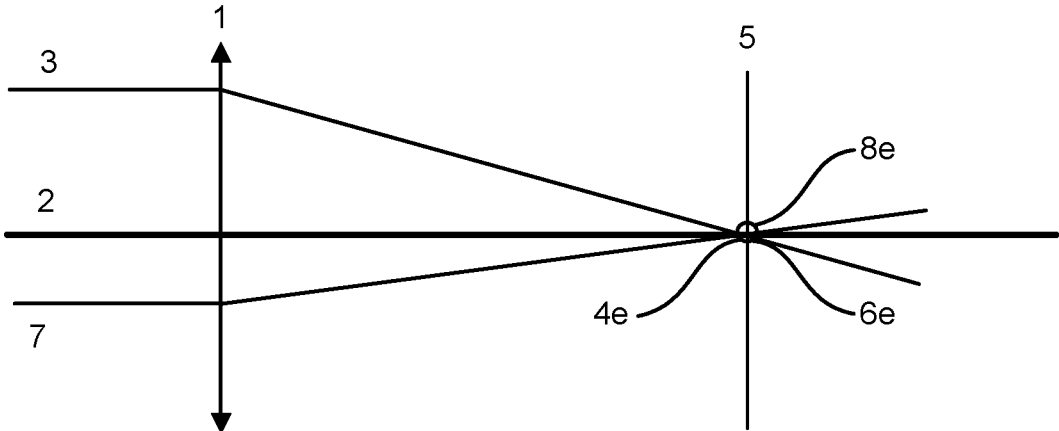
FIGS. 3A and 3B illustrate a basic method of reducing monochromatic aberrations and increasing depth of field using pupil size for an emmetropic eye.
Figure 3B:
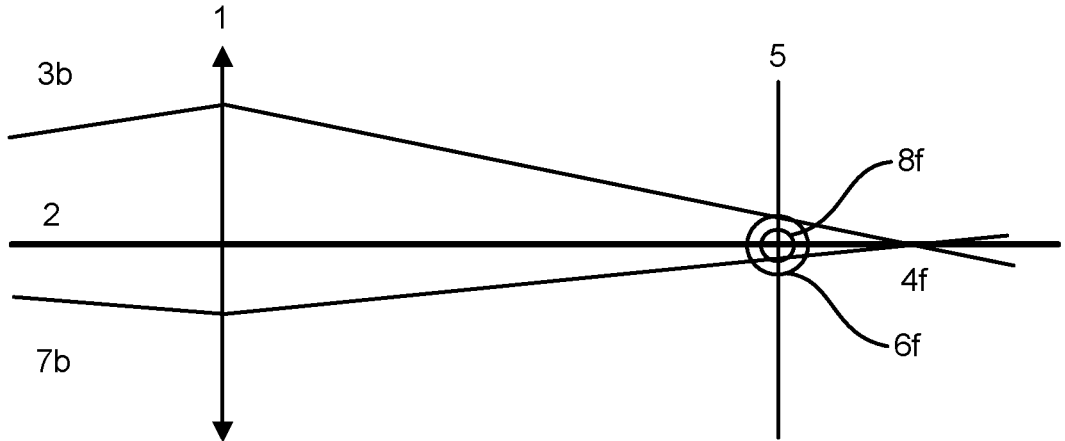

Similarly, FIGS. 3A and 3B (collectively referred to as FIG. 3) show that the same parallel ray height to blur circle diameter property holds for an emmetropic eye. For a distant object, the focal point 4e is now at the retina (since the eye is emmetropic) and the blur circles 6e and 8e have zero radius. For a closer object, the focal point 4f is behind the retina and blur circle 8f corresponding to ray 7b which is closer to the optic axis has a smaller diameter than blur circle 6f corresponding to ray 3b which is further from the optic axis.

In general, an eye has aberrations, which means that as an incident ray location changes, the focal point in the eye also changes. But regardless of where the focal points are located (in front of-, on-, or behind the retina), as incident ray heights are reduced so are the blur circle diameters on the retina. Stated another way, for a given amount of defocus (dioptric error) in the eye, vision is improved as the height of incident rays is reduced. This principle is used when someone squints causing the eyelids to block the incident rays further from the optic axis of the eye in an attempt to see an out-of-focus distant or near object more clearly.

Figure 4A:
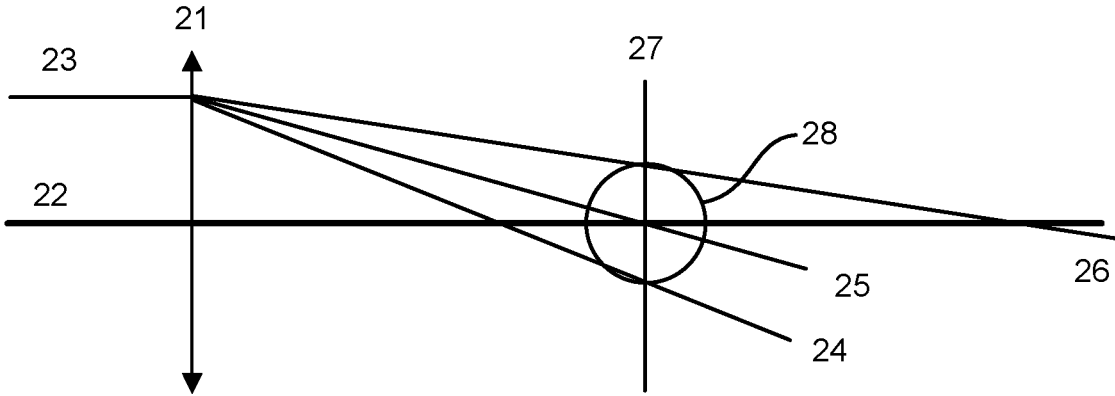
FIGS. 4A and 4B illustrate the basic method of reducing chromatic aberrations using pupil size.
Figure 4B:
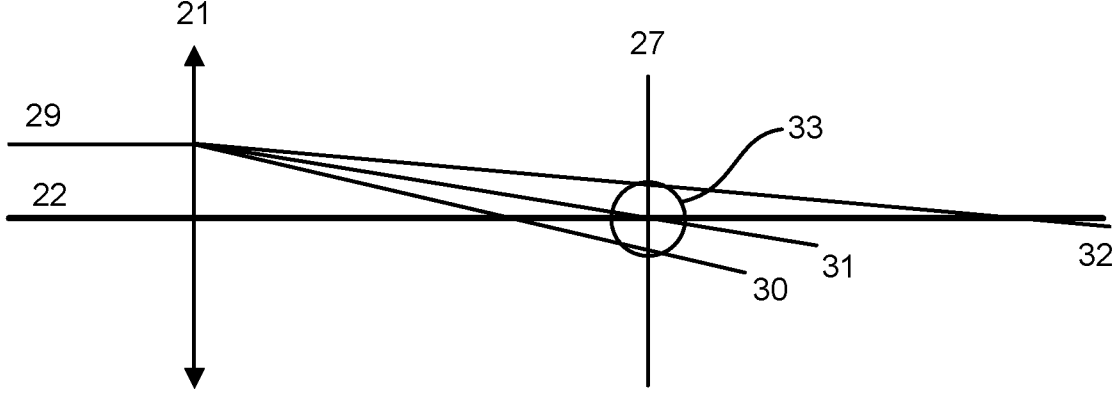

The ray tracing illustrated in FIGS. 1A-3B is for a single wavelength of incident light. For polychromatic light, multiple wavelengths are present. This is commonly illustrated by three rays of different wavelengths as shown in FIGS. 4A and 4B (collectively referred to as FIG. 4). It is well known that for the components of the eye and typical optical materials, as the wavelength of light increases, the refractive index decreases.

In FIG. 4A, a converging lens 21 has optical axis 22. An incident chromatic ray 23 consists of three wavelengths for blue (450 nm), green (550 nm), and red (650 nm) light which approximately span the range of visible light. Due to different indices of refraction for the three wavelengths, the blue light ray 24 is refracted more than the green light ray 25, and the green light ray is refracted more than the red light ray 26. If the green light ray is in focus, then it crosses the observation plane 27 at the optical axis. The chromatic spread of these three rays lead to a chromatic blur 28 on the observation plane.

In FIG. 4B, the incident chromatic ray 29 has a lower ray height than the chromatic ray 23 in 4A. This leads to smaller chromatic blur 33 at the observation plane. Thus, just as for the monochromatic blur of FIGS. 1A-3B, chromatic blur is decreased as the chromatic ray height is decreased. The situation in FIG. 4 can be related to the eye by considering converging lens 21 to be the principal plane of the eye and observation plane 27 to be the retina. The human eye normally has a large amount of chromatic aberration (about 1.0 to 1.2 diopters over the central visual range) so this reduction in chromatic aberration can be significant leading to a noticeable improvement in the eye's visual quality, especially as measured by its contrast sensitivity.

Taken together, FIGS. 1A-4B illustrate that decreasing ray height decreases both monochromatic and chromatic aberrations at the retina, thus increasing the quality of vision. This can be accomplished by either blocking rays with larger distance from the optical axis by decreasing the pupil diameter or by spreading light from these rays evenly and/or widely across the retina so that more aberrant rays contribute much less light to the central retinal blur circle. Another feature of this effect is that the depth of field is increased as the ray height is decreased as illustrated in FIGS. 1B, 2B, and 3B.

Figure 5A:
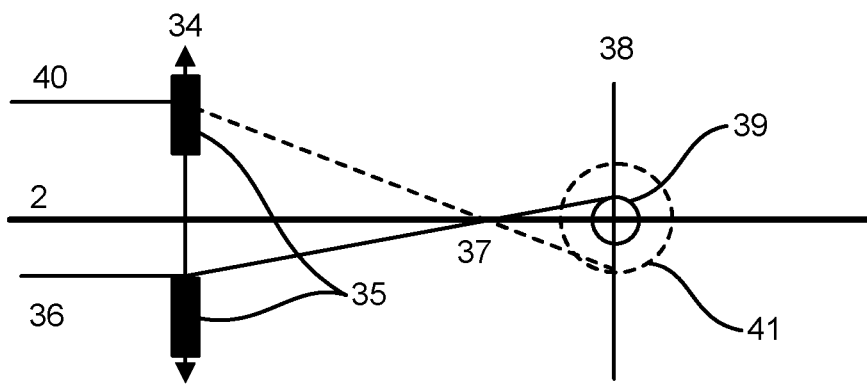
FIGS. 5A and 5B illustrate the basic concept of the virtual aperture to limit the effective pupil size.

FIG. 5A shows a converging lens 34 with optical axis 2 and aperture 35. Incident parallel ray 36 just clears the aperture and thus passes through the lens focal point 37 and intersects the observation plane 38. All parallel rays with the same height as ray 36 trace a small blur circle 39 on the observation plane. Incident parallel ray 40 is blocked by the aperture, and thus it cannot continue to the observation plane to cause a larger blur circle 41. In this way, an aperture which reduces the incident ray height reduces the blur diameter on the observation plane.

Figure 5B:
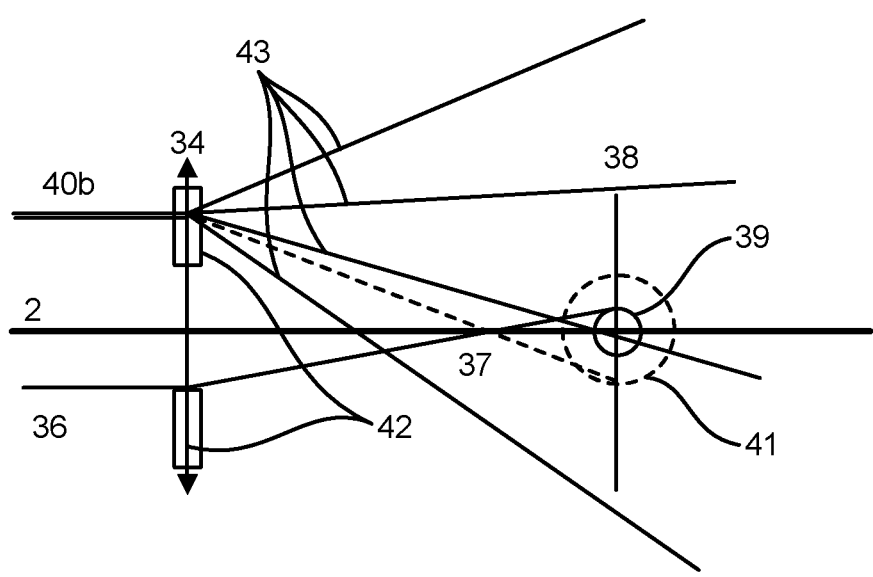

FIG. 5B illustrates a "virtual aperture". That is, it is not really an aperture that blocks rays, but the optical effect is nearly the same on central vision. In this figure, bundle of rays 40b incident on the virtual aperture propagate through the virtual aperture 42 and through refraction, diffraction, scattering, and/or reflection, yield rays 43 which are widely spread out so there is very little contribution to stray light (blurring light) at any one spot on the observation plane. This is a principal mechanism of operation of the disclosed IOL.

Exemplary Optical Layout of the IOL

FIGS. 6A-6C illustrate a layout of an example IOL that employs optical principles to achieve the benefits of decreased monochromatic and chromatic aberrations and increased depth of field. FIG. 6A shows a front view of the IOL wherein the front view may be an anterior view. FIG. 6B shows a back view of the IOL wherein the back view may be a posterior view. FIG. 6C shows a side view of the IOL. The IOL includes a central optical zone 46 (with back side 46b) that provides correction of defocus, astigmatism, and any other correction required of the lens such as spherical aberration. Generally, for an IOL using a virtual aperture, the central optical zone diameter is smaller than that of a traditional IOL. This leads to a smaller central thickness which in turns makes the IOL easier to implant and allows a smaller corneal incision during surgery. The IOL includes a virtual aperture 48 that is positioned further peripherally outward relative to the center location of the central optical zone 46. Moving peripherally outward from the virtual aperture 48, at least one IOL haptic 50 (with back side 50b) is located on the IOL. The haptic 50 can be formed of one or more arms that extend peripherally outward to define a peripheral most edge of the IOL. In an example, the optical zone has a diameter of 1.5 mm. The haptic 50 may define an outermost peripheral region of the IOL. A first plurality of light rays incident on an anterior optical surface of the optical zone can pass through the optical zone to form an image on a retina when the IOL is positioned in an eye, while a second plurality of light rays incident on an anterior virtual aperture surface are dispersed widely downstream from the IOL towards and across the retina, such that the image comprises an extended depth-of-field and further wherein the virtual aperture reduces monochromatic and chromatic aberrations in the image. The optical zone can comprise at least one of bifocal optics, trifocal optics and multifocal optics.

The virtual aperture is connected to the optical zone 46 by a first transition region 47, which is located at a peripheral edge of the optical zone 46 such that the virtual aperture is a first periphery region that surrounds or partially surrounds the optical zone. The haptic can comprise a second periphery region for positioning the intraocular lens within an eye. The first transition region is located peripherally outward of the optical zone 46. A second transition region 49 connects the haptic 50 to the virtual aperture 48. The first transition region 47 and the second transition region 49 are configured to ensure zero- and first-order continuity of an outer surface of the IOL on either side of the respective transition region. A common way to implement these transition regions is a polynomial function such as a cubic Bezier function. Transition methods such as these are known to those skilled in the art. On the back side of the IOL is a central optic zone 46*b*, a haptic 50*b*, and a transition 47*b* between them. FIGS. 6A-6C are not necessarily to scale, and the haptic shape is for illustration purposes only. Other haptic shapes and sizes known to those skilled in the art would be suitable as well. The first and second transition regions are not necessarily present per se in the IOL.

Figure 12:
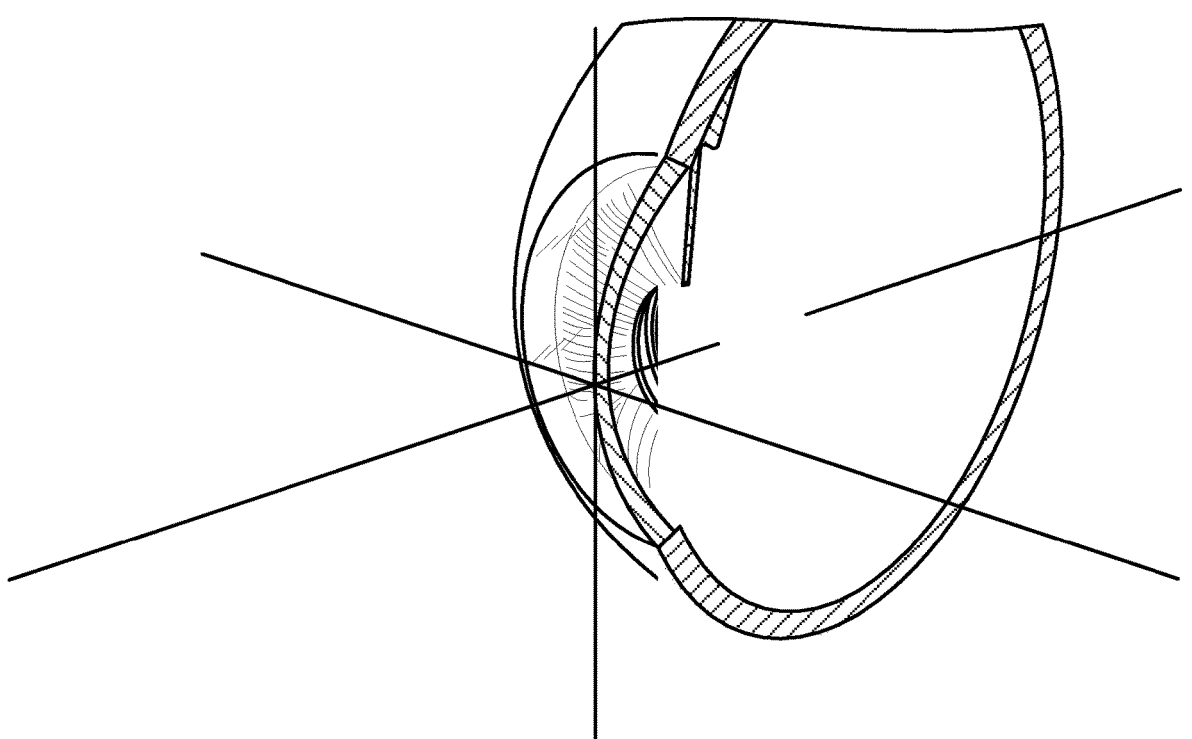
FIG. 12 shows an example embodiment of a ripple contour wherein a series of annular, concentric ripples are formed on the surface of a virtual aperture.

The IOL has an anterior surface and a posterior surface and the components of the IOL including the optical zone 46, the first transition region 47, the second transition region 49, the virtual aperture 48, the haptic 50 can each have a respective anterior surface and posterior surface. The optical zone 46 has an anterior optical surface that can include at least one multifocal zone and/or a toric region. At least a portion or region of the anterior surface and/or the posterior surface, such as in the region of the virtual aperture or other portion of the IOL, can have a surface contour or shape that achieves a desired or predetermined effect for light passing therethrough. In nonlimiting examples, the surface contour of the anterior surface and/or the posterior surface includes a region with a ripple-type contour such as a wave shape or an undulating shape that forms a series of raised and lowered surfaces. FIG. 12 shows an example embodiment of a ripple contour wherein a series of regions of annular, concentric ripples that are formed on the surface of a virtual aperture. The ripples can be, for example, annular corrugation or a series of annular corrugations that radiate outward from a center location.

Figure 13:
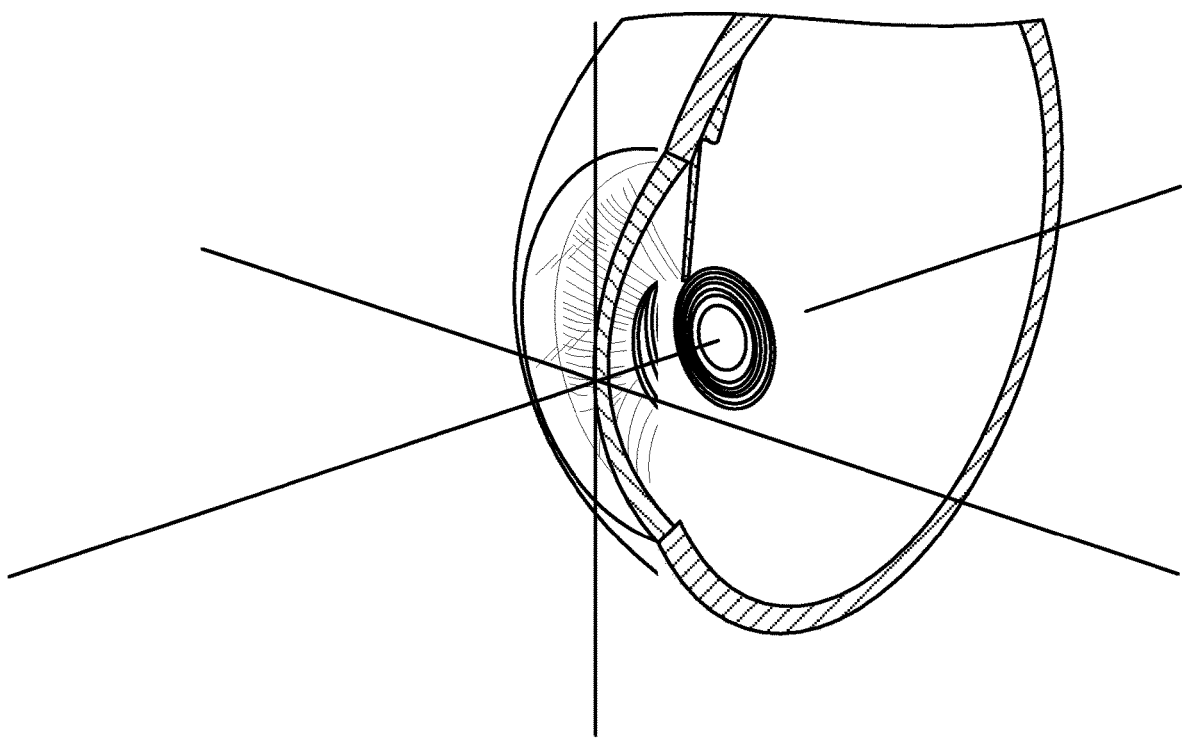
FIG. 13 shows an example embodiment of a micro-prism shape on the surface of the virtual aperture.
Figure 14:
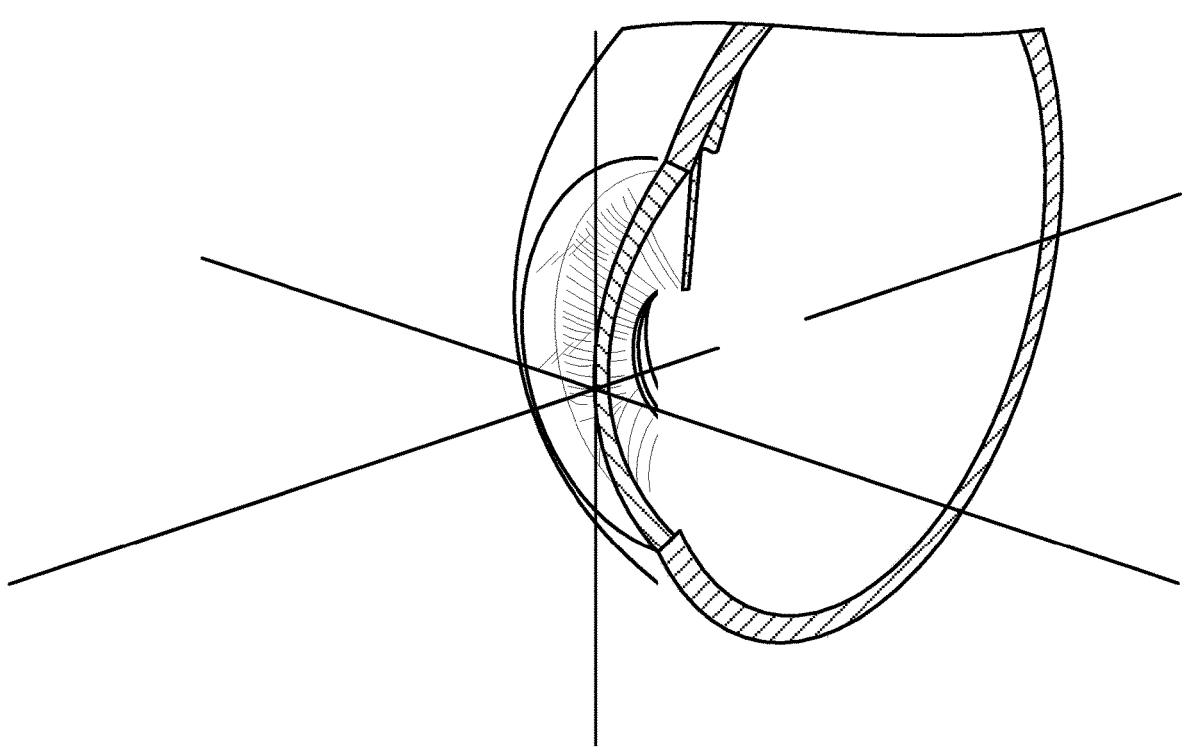
FIG. 14 shows an example embodiment of a smooth surface of the virtual aperture.

The ripples (or other surface contour) can be arranged in any of a variety of patters on the posterior surface and/or anterior surface of the IOL. In an embodiment, the surface contours are arranged in a series of concentric, annular (or partially annular) shapes, patterns, or regions that radiate from a central or other point on the IOL. In another embodiment, the surface contour can be a micro-prism shape or a series of microcrystalline shapes that are arranged on the surface. FIG. 13 shows an example embodiment of a micro-prism shape on the surface of the virtual aperture. The anterior and/or posterior surface can also be a smooth surface. FIG. 14 shows an example embodiment of a smooth surface of the virtual aperture. Some example embodiments of micro-prism configurations are described below.

Figure 28:
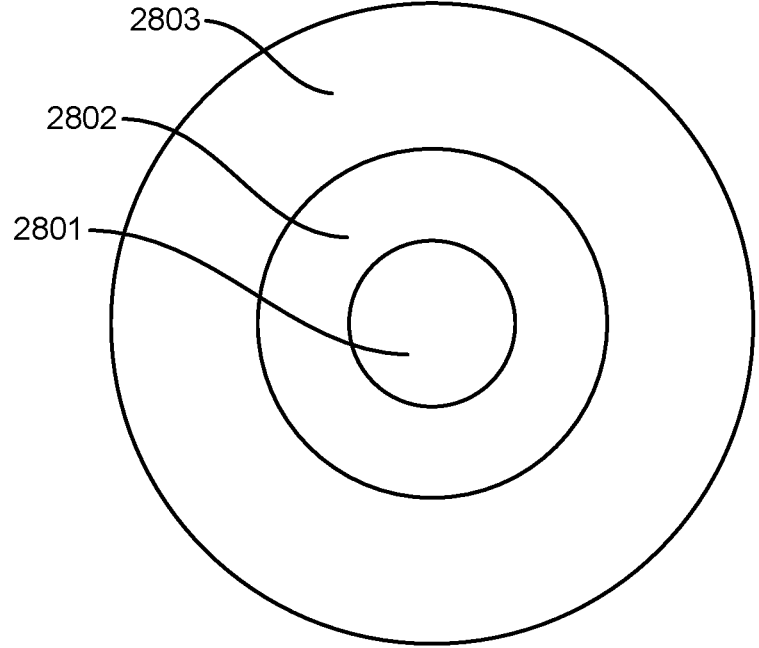
FIG. 28 shows a schematic representation of at least a portion of an IOL having a central optical zone surrounded by first and second annular regions.

The virtual aperture and/or micro-prism region can be present on the front and/or back surface of the IOL. In addition, it some applications it may be beneficial to have one annulus for a virtual aperture and one annulus for a micro-prism region. FIG. 28 shows an example of such an embodiment where the central optical zone 2801 is surrounded by a first annular region 2802 and that, in turn, is surrounded by a second annular region 2803. The first annular region can depict a ripple virtual aperture and the second annular region can depict a micro-prism region, or vice versa. The back surface can have a similar two annulus structure where the regions are the same as or reversed from the front surface. Additionally, the two annulus regions may or may not have the occupy the same extent from the center of the IOL. The IOL can have any quantity of annular regions with surface contours on its front or back surface.

In other applications, it may be beneficial to have more than two such annular regions on the front and/or back surface of the lens.

It should be appreciated that a wide variety of combinations of surface contours or smooth surfaces can be achieved between the anterior surface and the posterior surface of the IOL such as in the region of the virtual aperture. FIG. 15 shows a table with a variety of combinations of surface contours between the anterior surface and the posterior surface.

The surface contours can achieve various effects with respect to light passing through the IOL. For example, the surface contour can achieve a wide or wider spread of stray light depending upon the type of surface contour used. The surface contour can be used to achieve a spread of stray light which is guided away from a focal point of the retina.

Example Optic Zone Details

The optic zone(s) are configured to provide improved focused light rays for an eye. For most eyes, good vision is provided by implementing the improved spectacle correction, that is, the optic zone corrects sphere, cylinder, and axis errors for the eye. Together sphere, cylinder, and axis corrections are referred to as astigmatic corrections. In addition to the astigmatic error correction, there is an optimally reduced spherical aberration for the optical zone. Correcting for spherical aberration means that all or substantially all parallel incoming rays for the optical zone have the same focal point regardless of ray height. For an aphakic IOL, there is chosen the shape of the optical zone to have equal conic surfaces. Previous experience with this design shape and spherical aberration correction has shown it to be less sensitive to real-world positioning errors such as lens tilt and decentration with respect to the optical axis of the eye.

To determine the astigmatic power of the optic zone for correcting a particular eye's astigmatic error, a clinician uses an IOL power calculation procedure or algorithm. The IOL power calculation algorithm is either provided as a standalone program (such as a software program) or is part of an instrument that acquires some or all the eye measurements required to perform the IOL power calculations. These measurements typically include the cornea's optical power (keratometry), the anterior chamber depth (measured from cornea to the iris or crystalline lens), and the axial length (measured from cornea to retina). Once the measurements are entered into the IOL power calculation algorithm, the theoretical power of the IOL is calculated. Currently, one then selects an available IOL power (usually quantized in 0.5 diopter steps) that is close to the theoretical power for implantation into the eye.

Calculation of Apical Radius of Curvature R Per Meridian

To work well with the IOL power calculation algorithms, the labeled power of the disclosed IOLs are desirably accurate when placed in the eye. In general, the labeled power includes astigmatic powers which require the calculation of two principal powers at two orthogonal principal meridians. For an astigmatic correction written as $$\text{sphere+cylinder×axis}$$

where sphere and cylinder are in diopters and axis is in degrees (0 to 180), the two principal powers $P_1$ and $P_2$ are given by equation (1).

$$P_1 = \text{sphere}$$

$$P_2 = \text{sphere+cylinder} \tag{1}$$

In this equation, principal power $P_1$ acts along the meridian given by axis and principal power $P_2$ acts along the meridian given by (axis+90)modulo 180. To calculate the principal optic zone powers for an equal surface power shape, begin with the lens maker's formula given in equation (2).

$$PE = P + P - \frac{d}{n_{IOL} \times 1000}P^2 \tag{2}$$

US 12,575,924 B2

9

10

Given the principal lens power PE in diopters, the optic zone center thickness d in mm, and the index of refraction $n_{IOL}$ of the lens material (known to at least 3 decimal places), the surface principal power in diopters for the IOL optical zone is given by equation (3).

$$P = \frac{-B - \sqrt{B^2 - 4AC}}{2A} \qquad (3)$$

where $$A = \frac{d}{1000 \times n_{IOL}}$$

$$B = -2$$

$$C = PE$$

Figure 7:
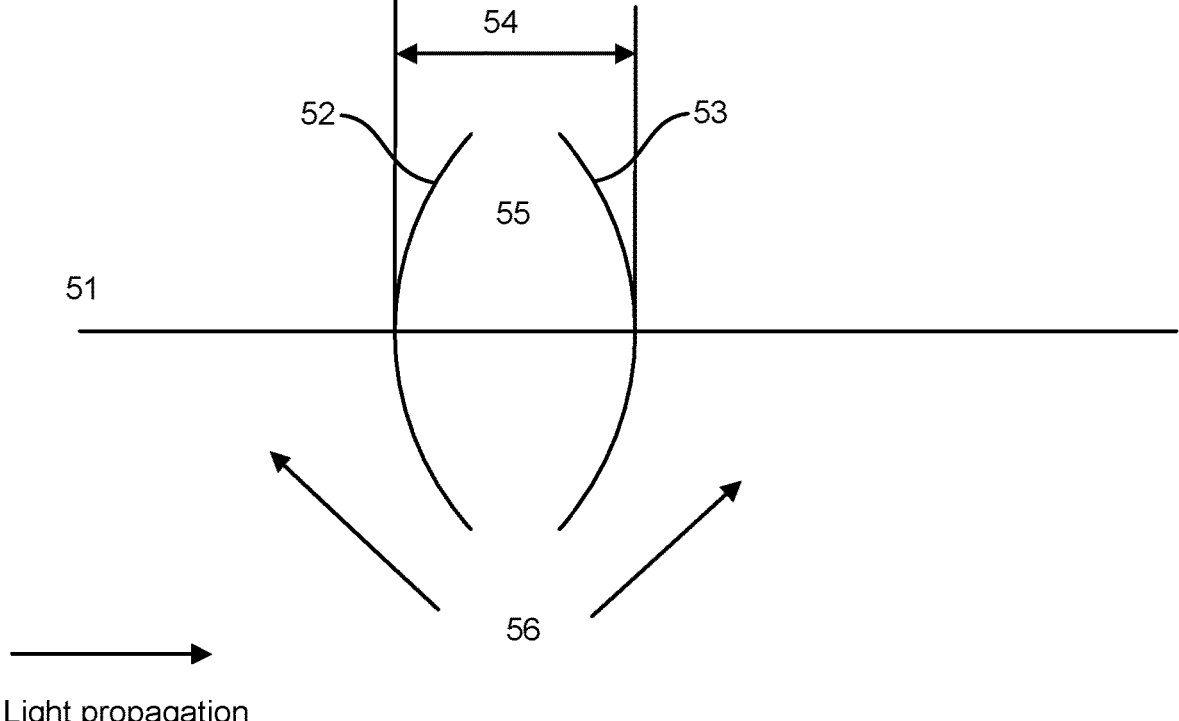
FIG. 7 illustrates the variables used in the calculation of the principal powers for the optic zone.

The primary parameters involved in the calculation of the surface powers $P_1$ and $P_2$ in diopters are schematically illustrated in FIG. 7. FIG. 7 schematically shows an optical axis 51 passing through the center of front (or anterior) surface 52 and back (or posterior) surface 53 of an optic zone of the IOL. The front and back surfaces 52 and 53 are equal, that is they are both conic curves with equal apical radius $R_a$ in mm and conic constant K. The front and back surfaces are separated in the center by the center thickness d in mm 54. The material of the lens has a known in situ index of refraction $n_{IOL}$ 55 and the medium surrounding the lens inside the eye has in situ index of refraction $n_{EYE}$ 56.

Once the principal powers $P_1$ and $P_2$ for the optic zone surface are obtained using equations (1)-(3), the powers for each meridian θ are calculated using equation (4).

$$P(\theta) = P_1 + (P_2 - P_1)[\sin(\theta - \text{axis})]^2 \qquad (4)$$

Then, given the power (diopters) in a meridian θ, the surface radius of curvature in that meridian R(θ) (mm) is computed using equation (5).

$$R(\theta) = 1000 \times \frac{n_{IOL} - n_{EYE}}{P(\theta)} \qquad (5)$$

In this equation,
$n_{IOL}$=the index of refraction for the IOL material
$n_{EYE}$=the index of refraction for the media inside the eye (1.336)
P(θ)=the power in meridian θ
R(θ)=the radius in meridian θ

Using equations (1)-(5) there can be calculated the equal toric optic zone surface, where each meridian θ has radius of curvature R(θ). If cylinder=0 in equation (1), then the radius is constant for each meridian, R(θ)=R.

Calculation of Optimized Conic Coefficient K Per Meridian

To provide a spherical aberration correction, each meridian profile is represented as a conic curve and optimize the conic constant K to optimally reduce spherical aberration. A conic curve [3] is given by equation (6).

$$y^2 - 2rx + (K+1)x^2 = 0 \qquad (6)$$

In this equation,
x=distance along the optical axis in mm, positive to the right
y=distance perpendicular to the optical axis in mm, positive up r=the apical radius of curvature in mm
K=the conic constant (dimensionless), for a circle K=0
Solving (6) for x gives an equation for the sag of the curve as shown in equation (7).

$$x = \frac{y^2/r}{1 + \sqrt{1 - (K+1)(y^2/r^2)}} \qquad (7)$$

The conic sag derivative is given in equation (8).

$$\frac{dx}{dy} = \frac{y}{\sqrt{r^2 - y^2(K+1)}} \qquad (8)$$

The analytic derivative in equation (8) could also be approximated numerically by those skilled in the art using a difference operator such as a forward-, backward-, or central-difference equation and could be a first- or higher-order difference equation. The derivative is used to compute the normalized tangent vector T(y) as shown in equation (9).

$$T(y) = \frac{\left[\begin{array}{c} \frac{y}{\sqrt{r^2 - y^2(K+1)}} \\ 1 \end{array}\right]}{\sqrt{1 + \frac{y^2}{r^2 - y^2(K+1)}}} \qquad (9)$$

As described below, this tangent vector is used to match the transition zones tangent vectors to provide first-order continuity between the transition zones and the curve profiles they connect.

Once the apical radius for given meridian R(θ) is obtained, the optimum conic constant K(θ) to minimize spherical aberration is computed. In a previous method (described in U.S. Pat. No. 7,350,918) of optimizing the conic constant for an equal conic IOL optic, a single conic constant was found for the entire surface by considering only a single meridian and a single ray height. The optimization was carried out using Newton-Raphson iteration to set the longitudinal ray aberration for this single meridian/ single ray height to zero. In the present case, a conic constant is optimized for each meridian. This optimization is performed using a dense set of incident ray heights along the meridian and finding the resulting ray height at an observation plane placed at the back focal point of the optical zone. The location of the back focal points in given in equation (10).

$$BFL = 1000 \frac{n_{EYE}(1000 \cdot n_{IOL} - P \cdot d)}{P(2000 \cdot n_{IOL} - P \cdot d)} \qquad (10)$$

In this equation,
$n_{IOL}$=the index of refraction for the IOL material
$n_{EYE}$=the index of refraction for the media inside the eye (1.336)
P=the power in meridian θ in diopters
BFL=the back focal length in mm
During optimization, an exhaustive search is performed over the conic constant K value to find the value that minimizes a cost function E. This cost function E is given in equation (11).

11

$$E = \left[ \frac{\sum_{n=0}^{N-1} y_0(n)|y_1(n)|^P}{\sum_{n=0}^{N-1} y_0(n)} \right]^{1/p} \quad (11)$$

In this equation, n=an indexer over the traced rays, (0 to N−1)

N=the number of rays traced $y_0(n)$=the height of the incident ray n at the front surface of the optic zone $y_1(n)$=the height of the ray n at the observation plane located at the back focal point p=transverse ray error power, a scalar controlling the behavior of the cost function In the cost function equation, the transverse ray error y1(n) is weighted by its corresponding incident ray height $y_0(n)$ to account for the optical sector area it represents. For an application, a suitable value for the transverse ray error power p is 3. This value is selected as a compromise between p=2 (which specifies the typical Euclidian norm and is associated with the RMS error) and p=∞ (which is for the maximum error or infinity norm). Selecting this value for p provides a superior error norm for an application because the largest transverse ray error values are smaller than in typical RMS optimizations, but still keeps most transverse ray error values smaller than the largest error that would be present in the infinity norm case. This exhaustive search optimization for K is performed over the range of K=(−1 to 0) with N=10,000 equally spaced incident ray heights so that the optimal K is found to 4 decimal places.

Figure 8:
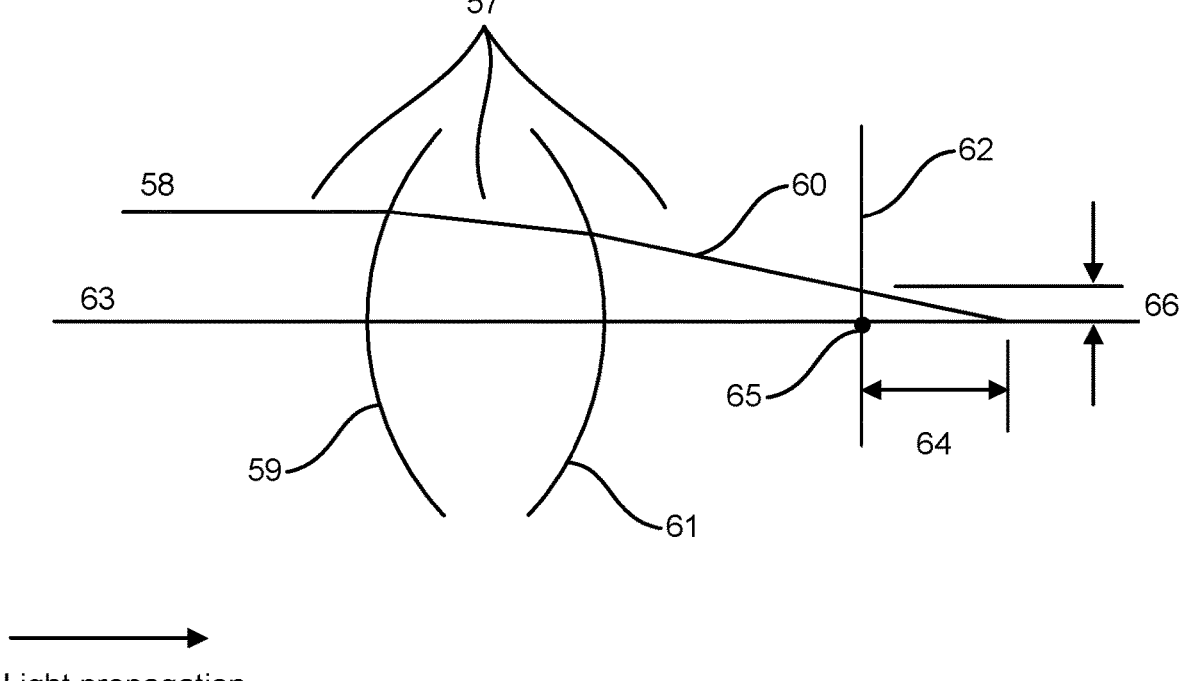
FIG. 8 illustrates a ray tracing procedure to optimize conic constant K for a given meridian.

FIG. 8 schematically illustrates a single ray 57 in this optimization calculation for an IOL. An incident ray 58 with ray height $y_0$ propagates from left to right into the optic zone front surface 59. As the emergent ray 60 exits the back surface 61 of the optic zone, it intersects the observation plane 62 and then the optical axis 63. The longitudinal ray error 64 is the distance from the focal point 65 to the emergent ray's intersection point on the optical axis. The transverse ray error 66 is the distance from the focal point 65 to the emergent ray's intersection point with the observation plane 62. The values used in the cost function equation are the height $y_0$ of the incident ray 58 and the height $y_1$ 66 of the emergent ray 60 as it intersects the observation plane 62.

An example range of values for this optical zone are as follows:

| Parameter | Units | Range | Preferred |
|---|---|---|---|
| Sphere | Diopters | 5.0 to 40.0 in steps of 0.5 | All |
| Cylinder | Diopters | 0.0 plus 1.0 to 6.0 in steps of 0.5 | All |
| Axis | Degrees | 1 to 180 in steps of 1 | All |
| Center thickness | mm | 0.4 to 1.0 | 0.6 |
| Optic zone diameter | mm | 1.3 to 4.0 | 1.5, 2.25, 3.0 |

Calculation of Optic Zone Diameter

The following are simple equations for estimating the acuity given the pupil diameter and spherical refractive error. They are given in equations (12 and 13).

$$A = kDE \quad (12)$$

$$A = \sqrt{1+(kDE)^2} \quad (13)$$

12

A=acuity in minutes of arc (A=Sd/20), that is, the minimum angle of resolution k=a constant determined from clinical studies, mean value of 0.65

D=pupil diameter in mm

E=spherical refractive error in diopters

Sd=Snellen denominator

The second equation is postulated as being more accurate for low levels of refractive error and gives a reasonable result when E=0, which gives A=1 min of arc or 20/20.

Solving (13) for E yields equation (14).

$$E = \frac{\sqrt{A^2-1}}{kD} \quad (14)$$

Equation (13) yields the acuity A given the range of depth of field (Ex 2) in diopters and the pupil diameter D. Equation (14) yields the range of depth of field in diopters given the acuity A and the pupil diameter D. For example, for:

Acuity of 20/40, A=40/20=2 min arc

D=3.0 mm k=0.65

$$E = \frac{\sqrt{2^2-1}}{0.65 \times 3.0} = 0.89$$

Depth of field=2E=1.8 D. Using (13), $$A = \sqrt{1+(0.65\times3.0\times0.89)^2} = 2$$

Note that these equations for acuity and depth of field are only approximations that do not include the effects of diffraction. Using A=2 (20/40 acuity), the following approximate depth of field values for three primary diameters are calculated:

| Pupil diameter (mm) | Approximate depth of field (diopters) (2×) |
|---|---|
| 1.5 | 1.78 (3.55) |
| 2.25 | 1.18 (2.37) |
| 3.0 | 0.89 (1.78) |

Virtual Aperture Details

The Following Variables are Defined for the Virtual Aperture IOL.

| Variable | Definition |
|---|---|
| CT | Center thickness |
| ET | Edge thickness |
| R(m) | Apical radius of curvature in meridian m |
| K(m) | Conic constant in meridian m |
| TF1W | Front transition region 1 width |
| VAFW | Front virtual aperture region width |
| TF2W | Front transition region 2 width |
| LD | Lens diameter |
| OZ | Optic zone diameter |
| TBW | Back transition region |

Figure 9:
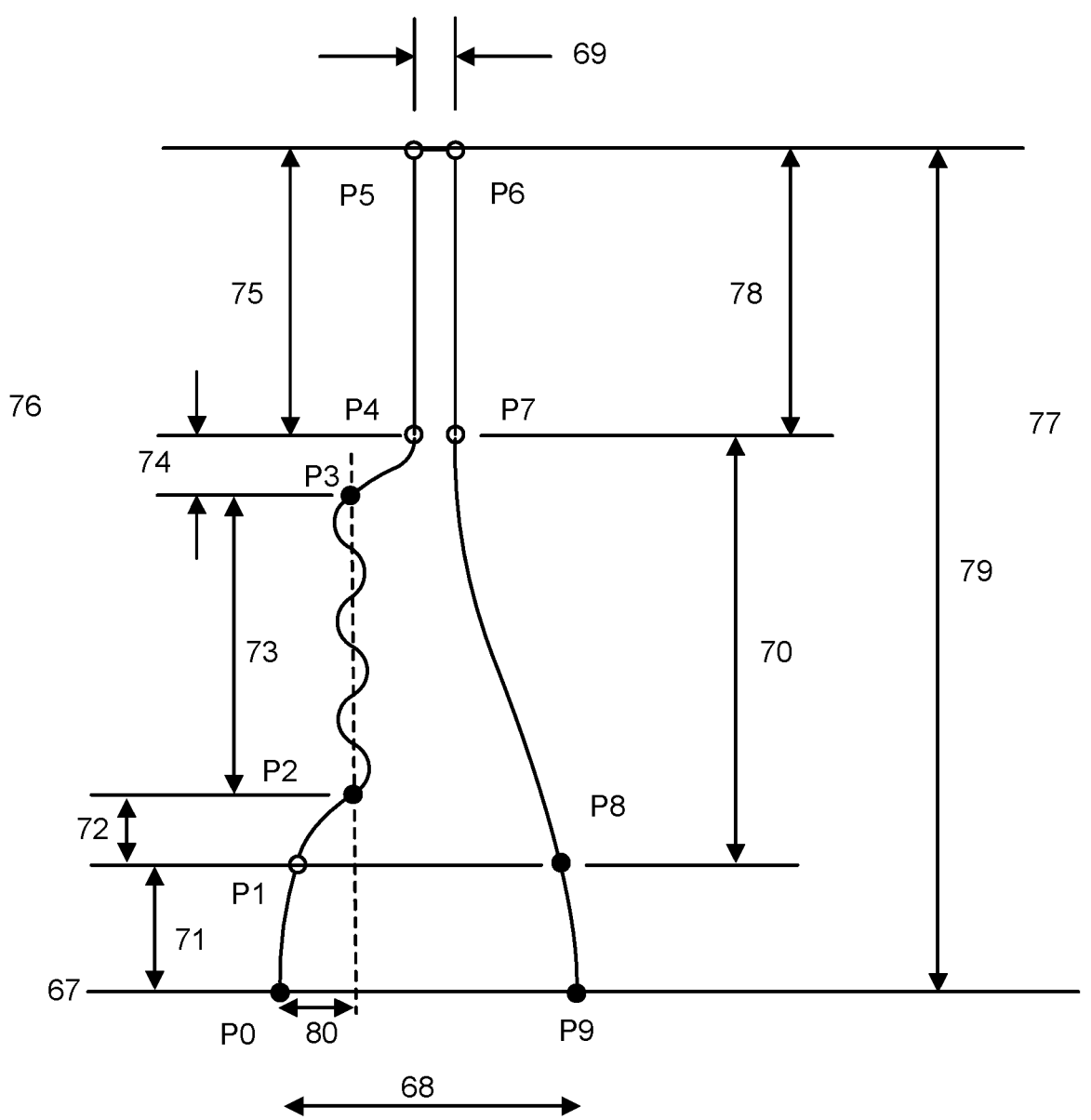
FIG. 9 illustrates specific points and distances for a meridian of the exemplary IOL profile.

The virtual aperture is entirely or partially responsible for spreading incident light rays which intersect the virtual aperture front surface widely across the retina. In an example embodiment the virtual aperture includes alternating high-power positive and negative profiles on the front surface and a smooth curve which connects the back surface of the optical zone to the haptic on the back surface. This is illustrated in FIG. 9. This figure shows the optical axis 67 of an IOL, center thickness 68, edge thickness 69 and surface landmark points P0-P9. The profile of FIG. 9 represents the top half of the IOL and is not necessarily drawn to scale. The front surface 76 shows the front optical zone between points P0 and P1 with optical zone semi-diameter (OZD/2) 71. The front surface first transition region has width 72 and is located between points P1 and P2. The virtual aperture has width 73 and is located between points P2 and P3. The front surface second transition region has width 74 and is located between points P3 and P4. The front haptic surface has width 75 and is located between points P4 and P5. The back surface 77 has back haptic surface width 78 and is located between points P6 and P7. The back surface transition region has width 70 and is located between points P7 and P8. The overall lens semi-diameter is 79. The location of the nominal virtual aperture reference line is 80.

The surface landmark points are located starting with P0=(0,0). In FIG. 9, X axis increases to the right and Y axis increases up. These points have the following coordinates:

Surface Landmark Points

| Point | X (mm) | Y (mm) |
|---|---|---|
| 0 | $x0 = 0$ | $y0 = 0$ |
| 1 | $x1 = \dfrac{y1^2 / R(m)}{1 + \sqrt{1 - (K(m)+1)(y1^2/R(m)^2)}}$ | $y1 = \dfrac{OZ}{2}$ |
| 2 | $x2 = \dfrac{CT - ET}{4}$ | $y2 = y1 + TF1W$ |
| 3 | $x3 = x2$ | $y3 = y2 + VAFW$ |
| 4 | $x4 = \dfrac{CT - ET}{2}$ | $y4 = y3 + TF2W$ |
| 5 | $x5 = x4$ | $y5 = \dfrac{LD}{2}$ |
| 6 | $x6 = x5 + ET$ | $y6 = y5$ |
| 7 | $x7 = x6$ | $y7 = y4$ |
| 8 | $x8 = CT - x1$ | $y8 = y1$ |
| 9 | $x9 = CT$ | $y9 = 0$ |

Figure 10:
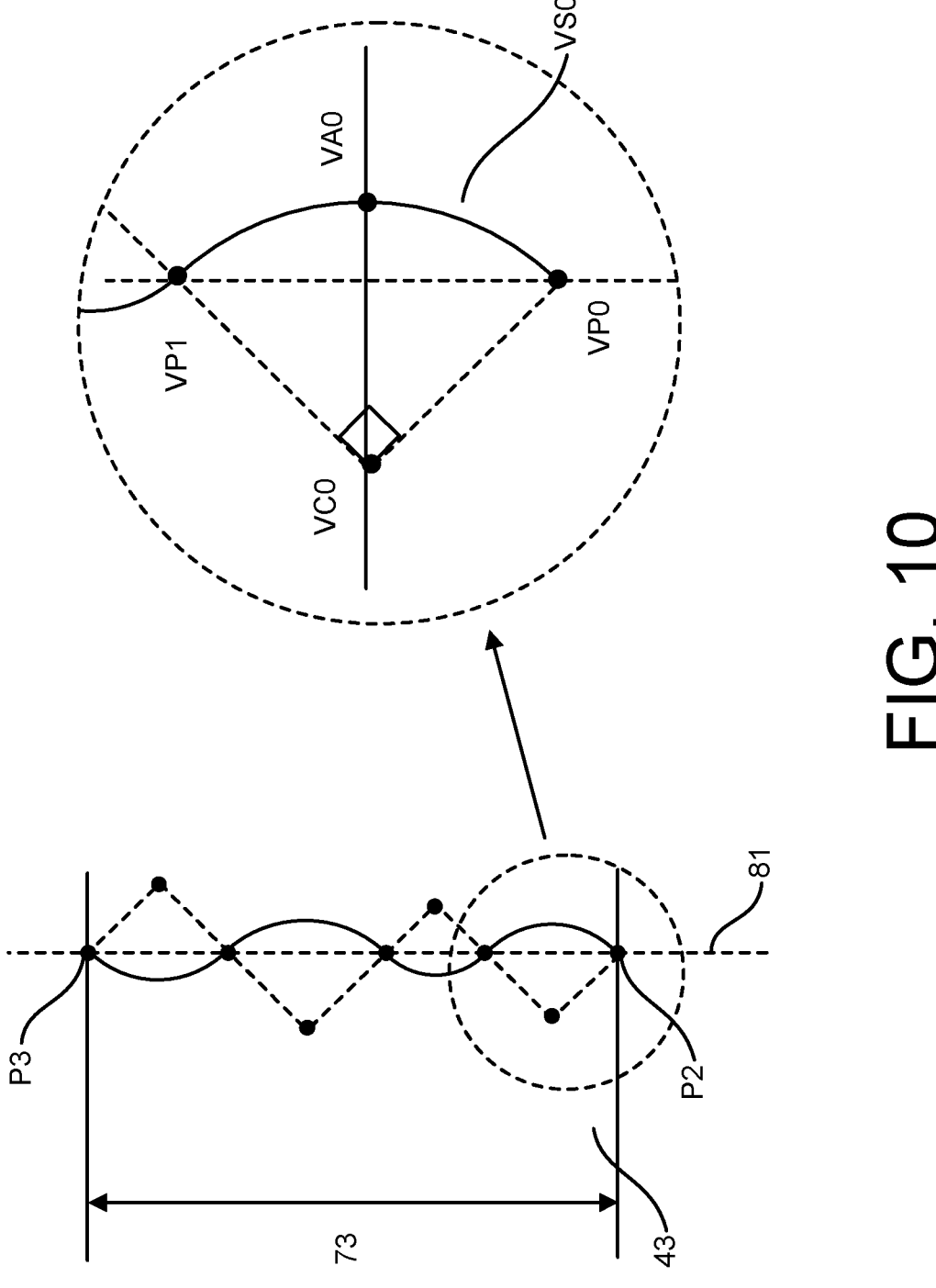
FIG. 10 illustrates details of the virtual aperture profile.

FIG. 10 shows details of the virtual aperture profile for an IOL, which is not necessarily drawn to scale. The virtual aperture 43 is shown in the left side of this figure as a continuous bold line of varying radius of curvature and starting at the bottom, alternating shape as concave/convex/concave/ . . . . The bottom point P2 in this figure corresponds to point P2 in FIG. 9. Likewise, the top point P3 in this figure corresponds to point P3 in FIG. 9. The bottom circular region on the left is encircled by a dashed circle and is magnified on the right side of this figure. In the magnified portion of the figure, there is shown a concave portion of a circle with surface profile VS0, center of the circle VC0, apex of the circle VA0, starting point of the circle VP0, and ending point of the circle VP1. The three points VP1:VC0:VP0 form a right angle as indicated by the little square at VC0. The virtual aperture nominal reference line 81 is a vertical line which contains the boundary points between alternating circle surface profiles VS0, VS1, etc. Knowing that this is a section of a circle with radius of curvature r0, the following vector relations are provided:

$$
VCj = \begin{cases} VPj + \dfrac{rj}{\sqrt{2}}\begin{bmatrix} -1 \\ 1 \end{bmatrix} & \text{for } j \text{ even} \\[2ex] VPj + \dfrac{rj}{\sqrt{2}}\begin{bmatrix} 1 \\ 1 \end{bmatrix} & \text{for } j \text{ odd} \end{cases} \tag{15}
$$

$$
VAj = \begin{cases} VCj + \begin{bmatrix} rj \\ 0 \end{bmatrix} & \text{for } j \text{ even} \\[2ex] VCj + \begin{bmatrix} -rj \\ 0 \end{bmatrix} & \text{for } j \text{ odd} \end{cases} \tag{16}
$$

$$
VP(j+1) = VPj + \begin{bmatrix} 0 \\ \sqrt{2}\,rj \end{bmatrix} \tag{17}
$$

In an example embodiment there are J, an even number, for example 14, alternating circle surface profiles in the virtual aperture profile. Each of these circle surface profiles VSj has its corresponding center VCj, starting surface point VPj, surface apex point VAj, ending surface point VP(j+1), and radius rj. Given the sequence of radii rj of length J and the width of the virtual aperture region VAFW, there is calculated a scale factor S such that if all radii are multiplied by S, the virtual aperture exactly fits its desired width. This scale factor is calculated using equation (18).

$$
S = \dfrac{VAFW}{\sqrt{2}\sum_{j=0}^{J-1} rj} \tag{18}
$$

After the scale factor is calculated, the sequence of rj values are multiplied by S to yield the set of radii used to determine the final virtual aperture profile. The preferred set of radii for the virtual aperture appear to be randomly selected in the range of 0.05 to 0.10 mm. With a virtual aperture width of 2.05 mm and an average of 0.075 mm radius per circle, there are about $$J=2.05/(0.075\times\sqrt{2})\approx18 \text{ circles.}$$

Example radii for the 18 circles that provide a virtual aperture width of 2.05 mm are listed below:

| J | Value |
|---|---|
| 0 | 0.060 |
| 1 | 0.071 |
| 2 | 0.095 |
| 3 | 0.081 |
| 4 | 0.109 |
| 5 | 0.070 |
| 6 | 0.102 |
| 7 | 0.078 |
| 8 | 0.065 |
| 9 | 0.068 |
| 10 | 0.119 |
| 11 | 0.067 |
| 12 | 0.060 |
| 13 | 0.091 |
| 14 | 0.096 |
| 15 | 0.070 |
| 16 | 0.087 |
| 17 | 0.063 |

Then, given the starting point P2 and the consecutive circle profiles, the circles for the virtual aperture profile are constructed that exactly fits the desired virtual aperture width.

In an alternative embodiment, the radii r for the consecutive circle profiles are equal and given the number of alternating circle surface profiles J and the width of the virtual aperture region VAFW the equal radii are given in equation (19).

$$r = \frac{VAFW}{J \times \sqrt{2}} \qquad (19)$$

Transition Regions Details

In an example embodiment, the front surface transition region of the IOL provide (1) a smooth blend between the outer edge of the front surface central optic zone and the inner edge of the front surface virtual aperture and (2) a smooth blend between the outer edge of the front surface virtual aperture and the inner edge of the haptic front surface. The back surface transition region provides a smooth blend between the outer edge of the back surface central optic zone and the inner edge of the haptic back surface. These transition regions can generate a set of surface points for the lathe file or other manufacturing device, such as a laser.

To smoothly blend or connect various regions of the lens, that is, to provide at least zero- and first-order continuity between these regions, cubic Bezier curves are employed. The smoothness of the transition regions can prevent visual artifacts. The parametric Bezier curve F(t) in two (and three) dimensions is given in equation (20).

$$F(t) = \sum_{i=0}^{n} \binom{n}{i} t^{i}(1-t)^{n-1} p_i \qquad (20)$$

where
n=order of Bezier curve, for cubic order, n=3
t=parametric variable goes from 0 to 1 as the curve goes from the first to the last control point
$p_i$=control points The blend function employed here is a cubic Bezier curve, so there are 4 points numbered $p_0$ to $p_3$. The width of the transition region (in degrees) is given by a variable $W_T$. The cubic Bezier curve passes through points $p_0$ at t=0 and $p_3$ at t=1. When end points $p_0$ to $p_3$ are set to be equal to the last points in the surfaces being connected by the transition region (for example, points P1 and P2 in FIG. 9), zero-order continuity is guaranteed. The derivative of the curve at point $p_0$ is equal to the slope of the line from $p_0$ to $p_1$. The derivative of the curve at the point $p_3$ is equal to the slope of the line from $p_2$ to $p_3$. Thus, it can be important to place control point $p_1$ along the line that passes through point $p_0$ (end of the curve at the previous region) and has slope equal to the slope at $p_0$ form the previous curve. Similarly, for the placement of point $p_2$. These constraints on control points $p_1$ and $p_2$ ensure first-order continuity at the edge of the regions being connected by the transition curve.

The four Bezier control points form a convex hull for the Bezier curve. The influence of the intermediate control points $p_1$ and $p_2$ on the shape of the curve is increased and decreased as the distance from the boundary points $p_0$ and $p_3$ is modified. A parameter $F_T$ (transition fraction) is used to control the placement of these intermediate control points within the blend region.

A small $F_T$ value (e.g., 0.1) keeps the intermediate control points $p_1$ and $p_2$ near their respective end control points $p_0$ and $p_3$. The small $F_T$ value does not maintain the blend curve derivative at the endpoints very far into the blend region. A larger $F_T$ value (e.g., 0.5) pushes the intermediate control points near the middle of the blend region. The larger $F_T$ value maintains the blend curve derivative at the endpoints further into the blend region. In this way $F_T$ can control the character of the transition curve inside the blend region.

To optimize or otherwise improve the transition curve for smoothness and therefore, prevent visual artifacts, the transition region cubic Bezier may have minimum curvature at all points along the curve in addition to maintaining zero- and first-order continuity at the endpoints as described above. The curvature of the cubic Bezier curve is calculated using equation (21).

$$C(t) = \frac{\|F'(t) \times F''(t)\|}{\|F'(t)\|^3} \qquad (L)$$

Equation (21) states that the curvature C(t) at the point given by the parametric variable t is the norm of the cross-product of the first- and second-derivatives divided by the norm of the first-derivative cubed. The cubic Bezier vector function and its first- and second-derivatives are given in equations (22), (23), and (24).

$$F(t)=(1-t)^3 p_0+3(1-t)^2 t p_1+3(1-t)t^2 p_2+t^3 p_3 \qquad (22)$$

$$F'(t)=-3(1-t)^2 p_0+3(t-1)(3t-1)p_1+(6t-9t^2)p_2+3t^2 p_3 \qquad (23)$$

$$F''(t)=(6-6t)p_0+(18t-12)p_1+(6-18t)p_2+6t p_3 \qquad (24)$$

In these equations, $p_0$ to $p_3$ are the four control points for the cubic Bezier. As described above, points $p_1$ and $p_2$ are selected so that the first-order derivatives at end points $p_0$ and $p_3$ match the regions to be connected. There is defined the normalized tangent vectors at $p_0$ and $p_3$ using equations (25) and (26).

$$T_0 = \frac{p_1 - p_0}{\|p_1 - p_0\|} \qquad (25)$$

$$T_3 = \frac{p_3 - p_2}{\|p_3 - p_2\|} \qquad (26)$$

These normalized tangent vectors could also be arrived at by directly evaluating the neighborhoods of the regions to be blended at points $p_0$ and $p_3$. Then, in a search for the minimum curvature cubic Bezier curve, the interior control points $p_1$ and $p_2$ are set according to equations (27) and (28).

$$p_1 = p_0 + frac \times s \times T_0 \qquad (27)$$

$$p_2 = p_3 - frac \times s \times T_3 \qquad (28)$$

Figure 11A:
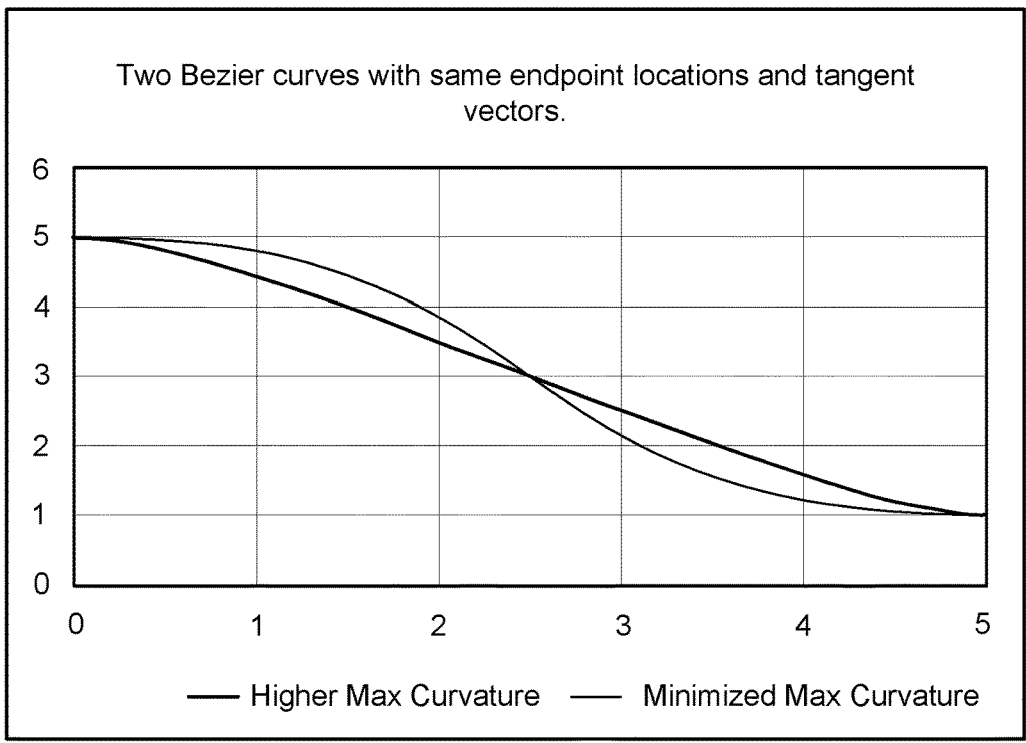
FIGS. 11A and 11B illustrate cubic Bezier curves and the results of minimizing curvature along the curves.

In these equations, s is the distance between endpoints $p_0$ and $p_3$, and frac is a scalar value between (0, 1) to be found that minimizes the curvature in equation (20) for all points along the Bezier curve. To further explain with an example, two Bezier curves with endpoint locations $p_0$ and $p_3$ and tangent vectors $T_0$ and $T_3$ are shown in FIG. 11A. One has significantly more curvature than the other, and the other has been optimized to have the smallest maximum curvature.

17

Figure 11B:
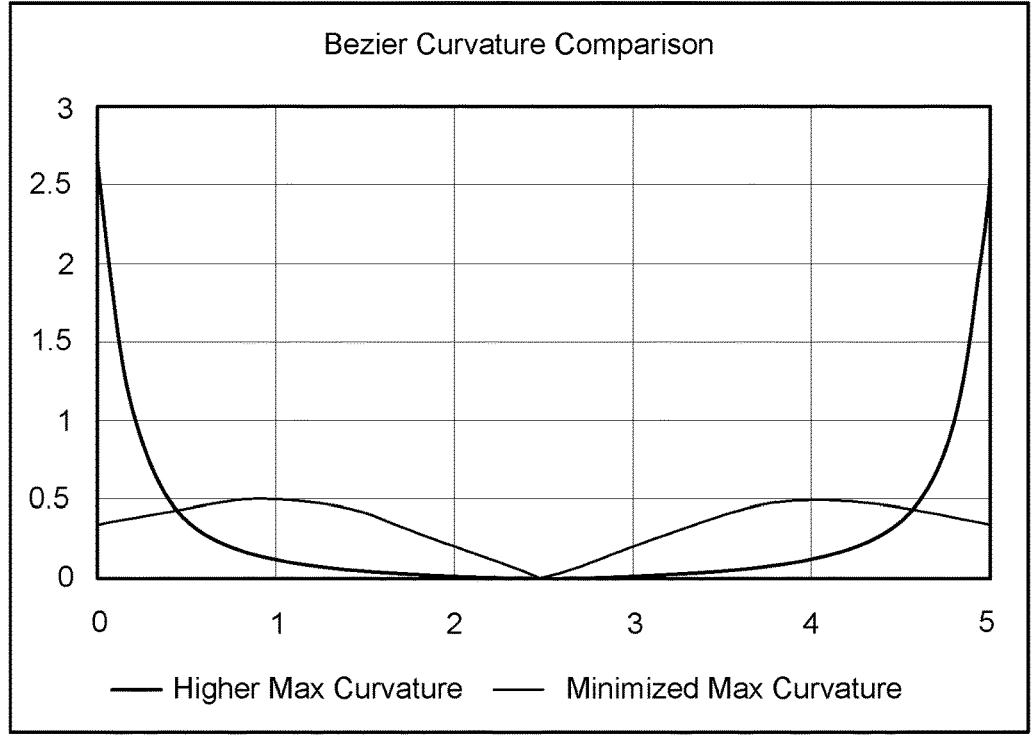

The corresponding curvature graphs are given in FIG. 11B. FIG. 11B shows that the un-optimized Bezier has a maximum curvature of around 2.6 while the optimized Bezier curve has a maximum curvature of around 0.5. This corresponds to a radius of curvature of 0.4 for this high curvature Bezier and 2.0 for the optimized Bezier curve. Not only does this lead to a smoother transition curve with minimal visual artifacts, it also allows the lathe cutting tool to have a radius five times larger than for the curve with the larger curvature.

To summarize the calculation of the Bezier curve transition zones, the following steps are performed:

Set the endpoints $p_0$ and $p_3$ to the corresponding endpoints of the equations of the surface profiles to be connected.

Compute the tangent vectors $T_0$ and $T_3$ at the endpoints using the equations of the surface profiles to be connected.

Perform an exhaustive search in the range of [0, 1] for frac to minimize the curvature C(t) over the range [0,1].

Use the optimized frac value to compute the interior points $p_1$ and $p_2$.

Use the four Bezier points $p_0$ to $p_3$ to compute the transition curve profile using equation (22).

The virtual aperture could be located on the back of the IOL instead of the front or the virtual aperture could be located on both the front and back surfaces of the IOL. The same is true of the micro-prism region. The optic zone illustrated in FIG. 1 is bi-convex, but the optic could be meniscus shaped or bi-concave, depending upon the desired optical power of the lens and its use as either a phakic or aphakic IOL.

Example Micro-Prism Virtual Aperture Structure

Figure 16:
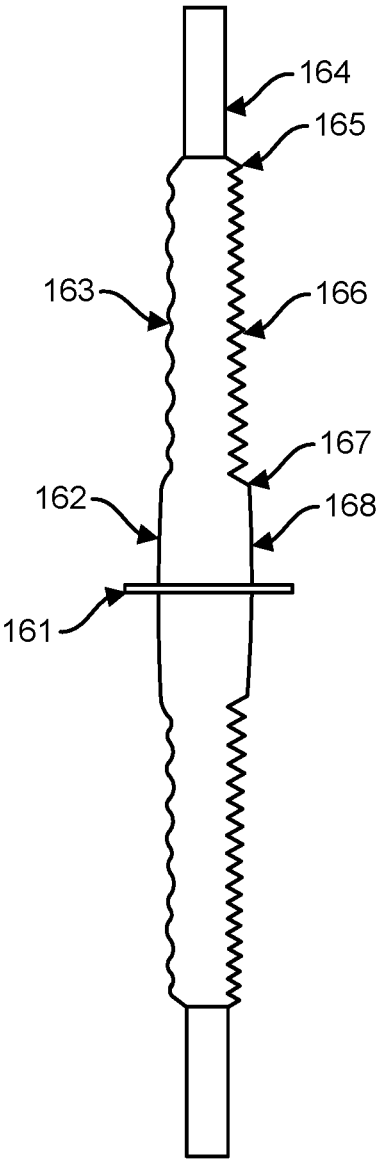
FIG. 16 shows a side view profile of an IOL with an anterior ripple virtual aperture and a posterior micro-prism region.

An example profile of an extended depth of focus IOL is illustrated in FIG. 16, which shows a side view of an IOL lens, which is symmetric about a horizontal, middle axis. The IOL has a front surface and a back surface. Due to its symmetry, only the top half of the lens is described. The lens profile has an optical axis 161 through the center of the lens. The front surface has a front optical zone 162, a ripple virtual aperture zone 163, and a haptic 164. The back surface has a transition zone 165 connecting a micro-prism region 166 to the haptic 164, the micro-prism region 166, a transition zone 167 connecting the micro-prism region 166 to the optical zone 168, and a back optical zone 168.

Figure 17:
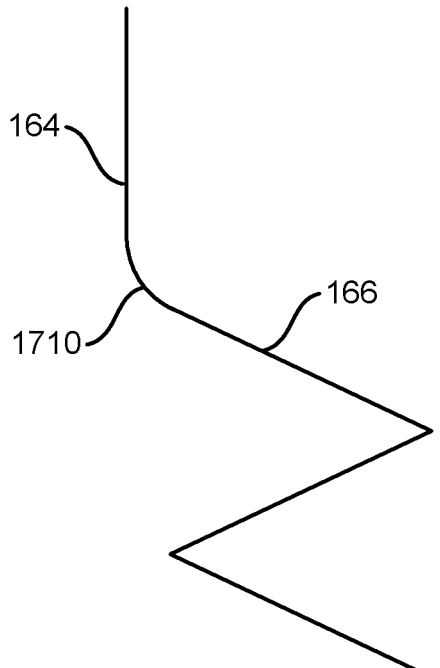
FIG. 17 shows a close-up of the micro-prism to haptic transition region of the IOL.

FIG. 17 shows an example contour of the transition zone connecting the micro-prism region 166 to the haptic 164. An edge of the haptic 164 is connected to a peripheral-most section of the micro-prism region 166 by fillet 1710 having at least one of a curved, rounded or circular contour.

Figure 18:
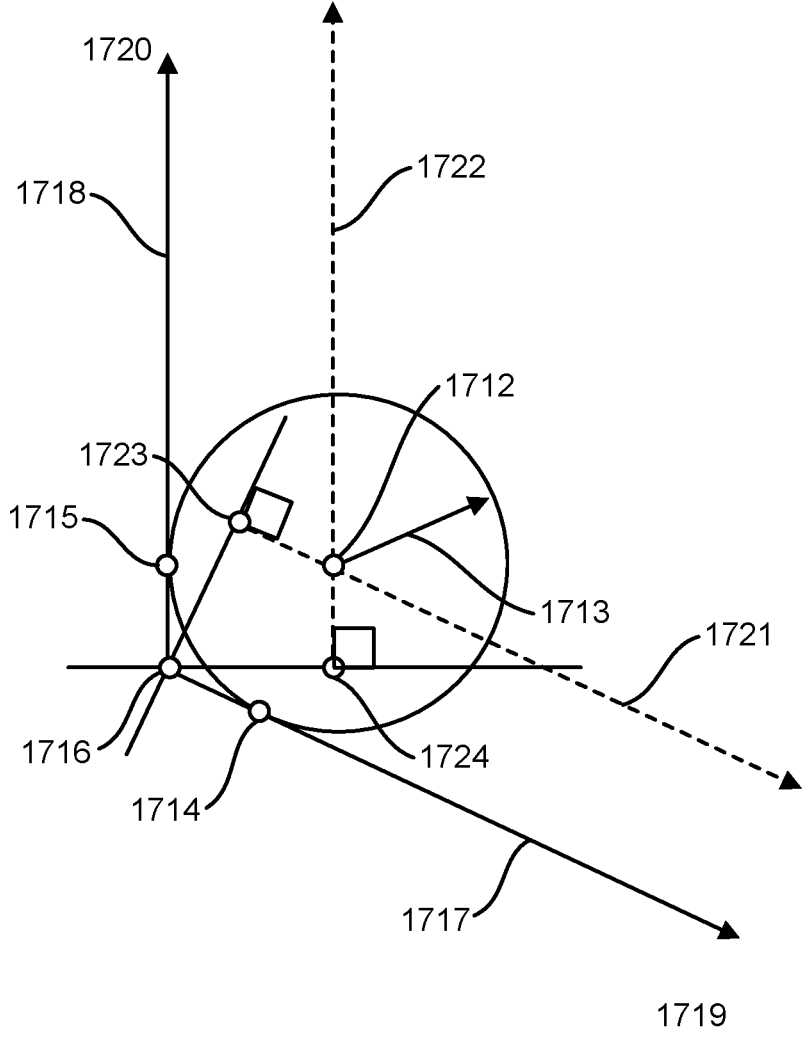
FIG. 18 shows an example geometry of a micro-prism to haptic transition fillet.

FIG. 18 shows geometric details of an example circular fillet 1710. The circular fillet 1710 is specified by its center 1712, radius 1713, start point 1714 and end point 1715. To calculate the fillet specification, there is provided the fillet radius, the intersection point 1716 of the line segments 1717 and 1718 to be connected by the fillet, and unit length direction vectors 1719 and 1720 parallel to line segments 1717 and 1718, respectively. We denote these given data as:

r=fillet radius, a scalar

P=intersection point of line segments, a length 2 vector $D_0$, $D_1$=unit length direction vectors parallel to line segments, length 2 vectors Rays 1721 and 1722 parallel to line segments 1717 and 1718, respectively, are constructed as follows.

$$R_n = P_n + t_n D_n \qquad (29)$$

18 where $$P_0 = P + r\begin{bmatrix} 0 & -1 \\ 1 & 0 \end{bmatrix} D_0$$

$$P_1 = P + r\begin{bmatrix} 0 & 1 \\ -1 & 0 \end{bmatrix} D_1$$

Here, each ray is defined by a starting point and a unit length direction vector. The ray starting points $P_0$ and $P_1$ are identified as items 1723 and 1724 in FIG. 18. The intersection point of these two rays is the center 1712 of the fillet circle. This intersection point 1712 is found by solving for the parameter $t_0$ or $t_1$ from equation (30) and then substituting this value into the ray equation (29) above.

$$\begin{bmatrix} t_0 \\ t_1 \end{bmatrix} = [D_0 \ -D_1]^{-1}(P_1 - P_0) \qquad (30)$$

In equation (30), the columns of the 2×2 matrix on the right-hand side contains the vectors $D_0$ and $-D_1$. We denote the center of the circle C. The remaining fillet specifications, points $P_a$ and $P_b$ corresponding to items 1714 and 1715 in FIG. 18, respectively, are calculated using equation (31).

$$P_a = C - r\begin{bmatrix} 0 & -1 \\ 1 & 0 \end{bmatrix} D_0 \qquad (31)$$

$$P_b = C - r\begin{bmatrix} 0 & 1 \\ -1 & 0 \end{bmatrix} D_1$$

The fillet circle connecting the micro-prism region to the haptic region is configured to provide a smooth transition to prevent visual artifacts that can exist at this location in some abrupt designs. Other methods can be utilized for this smooth transition as well such as a Bezier curve known to those skilled in the art.

Figure 19:
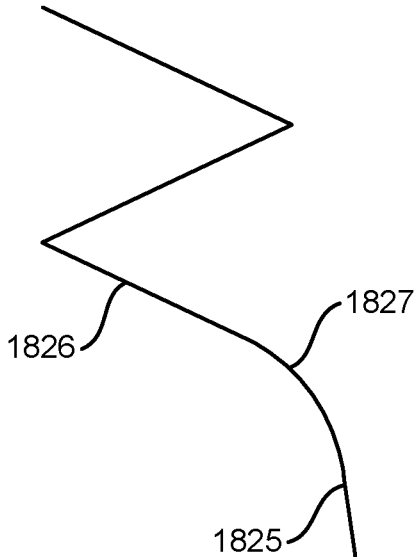
FIG. 19 shows a close-up of the micro-prism to optic zone transition region.

FIG. 19 shows an example geometry of a transition zone connecting the micro-prism region to the optic zone. An edge of the optic zone 1825 is connected to the first section of the micro-prism region 1826 by a circular fillet 1827.

Figure 20:
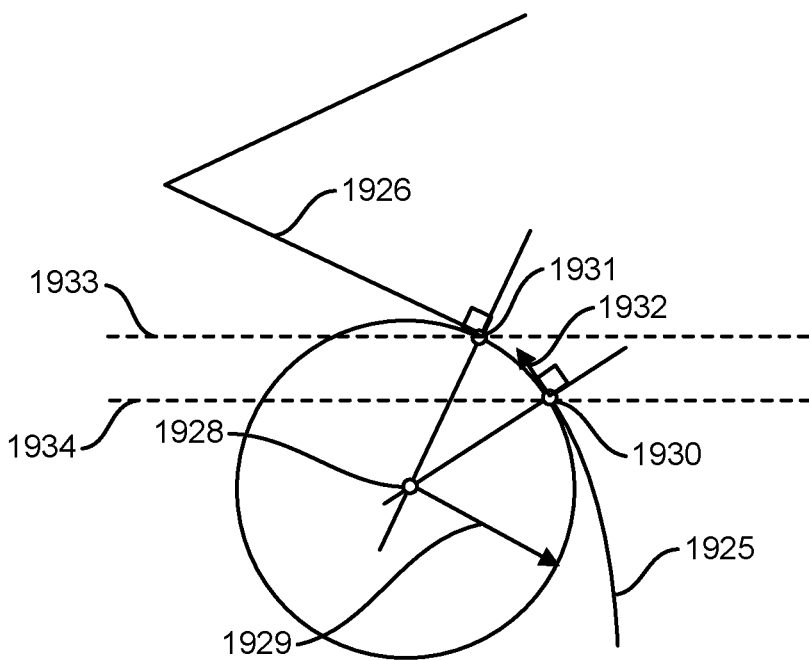
FIG. 20 shows a geometry of the micro-prism to optic zone transition fillet.

FIG. 20 shows details of the circular fillet connecting the optic zone to the micro-prism region. The circular fillet is specified by its center 1928, a radius 1929, a start point 1930 and an end point 1931. To calculate the fillet specification, there is provided the fillet radius, the start point 1930 at the edge of the optical zone to be connected by the fillet, unit length tangent vector 1932, and the slope of the micro-prism segment 1926. Given data is denoted as:

r=fillet radius, a scalar $P_a$=start point, a length 2 vector

T=unit length tangent vector continuing with the same slope as the end point of the optic zone, a length 2 vector s=slope of the micro-prism segment, a scalar The tangent vector T can be calculated analytically from an equation representing the optical zone profile, such as a conic equation, or numerically using a difference equation. The difference equation could be a forward-, backward-, or central-difference equation and could be a first- or higher-order difference equation. For example, if the optical zone has a circular profile, which could represent either a stigmatic or astigmatic optic zone, with center on the optical axis at point $C_o$, then the unit length tangent vector T is given by equation (31b).

19

$$T = \begin{bmatrix} 0 & -1 \\ 1 & 0 \end{bmatrix} \times \frac{P_a - C_o}{\|P_a - C_o\|}$$  (31b)

Also illustrated in FIG. 20 are the dashed line 1933 and dashed line 1934. The region below line 1934 is the optic zone, the region above line 1933 is the micro-prism zone, and the region between the line 1933 and line 1934 is the transition zone realized as a fillet circle. The center of the fillet circle C 1928 is found using equation (32).

$$C = P_a + r \begin{bmatrix} 0 & -1 \\ 1 & 0 \end{bmatrix} T$$  (32)

To find the fillet specification end point 1931, there is located the point on the circle where the slope of micro-prism segment 1926 matches the slope of the fillet circle. The coordinates of this end point 1931 are given by equations (33a) and (33b).

$$x_b = C.x + \frac{r}{\sqrt{\frac{1}{s^2+1}}}$$  (33a)

$$y_b = C.y + \sqrt{r^2 - (x_b - C.x)^2}$$  (33b)

The fillet circle connecting the micro-prism region to the optic zone is intended to provide a smooth transition to prevent visual artifacts that can exist at this location in some abrupt designs. Other methods can be utilized for this smooth transition as well such as a Bezier curve known to those skilled in the art.

In an example embodiment, the micro-prism array profile is placed on the back surface of the IOL. The micro-prism profile functions using a combination of refraction for some rays, total internal reflection for other rays, and some rays will be both refracted and total internal reflected. In the following discussion the micro-prism array profile is situated on the back surface of the IOL and light is travelling from left to right, that is, into the eye.

Figure 21:
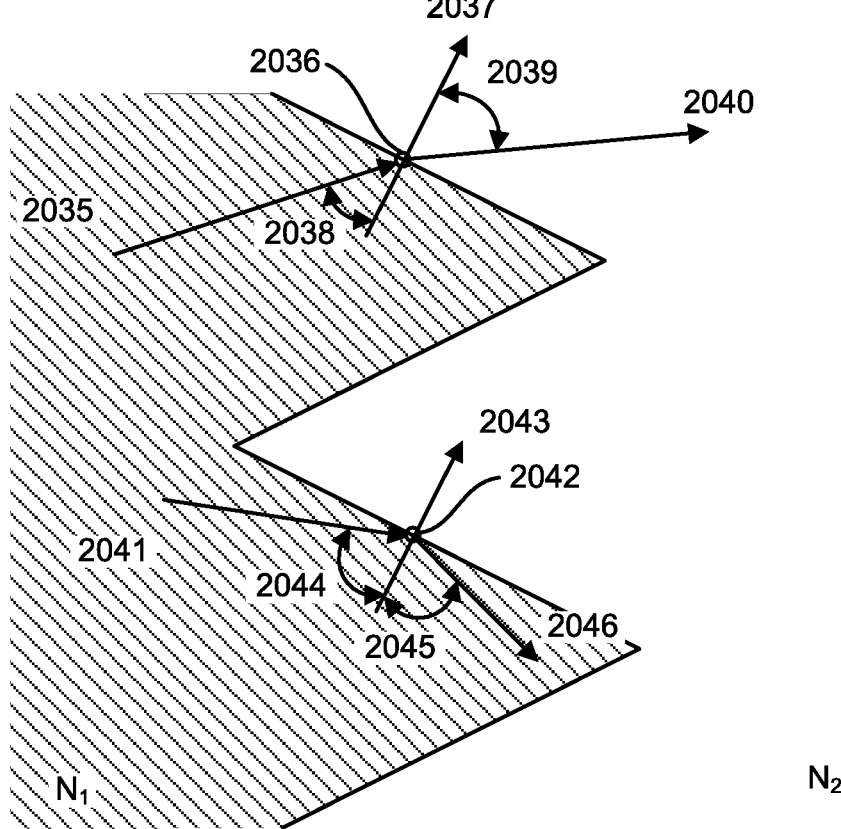
FIG. 21 shows a ray refraction and ray total internal reflection at the back surface of the micro-prism region.

FIG. 21 shows an example of a basic micro-prism array profile. The shaded portion of the array represents the inside of the IOL and the front surface of the IOL is not represented. The index of refraction $N_1$ inside the IOL is greater than the index of refraction $N_2$ outside the IOL. Typical values for $N_1$ and $N_2$ are 1.459 and 1.336, respectively. A light ray 2035 intersects the micro-prism surface at intersection point 2036 which has a surface normal 2037. This incident ray 2035 makes an incident angle 2038 with respect to the surface normal 2037. Snell's law describes how the light ray 2035 is refracted at the intersection point 2036 and is given in equation (34).

$$N_1 \sin(A_1) = N_2 \sin(A_2)$$  (34)

In this equation the incident angle is $A_1$ and the refracted angle is $A_2$. In the figure, $A_1$ corresponds to item 2038 and $A_2$ corresponds to item 2039. For example, using the typical values for $N_1$ and $N_2$, if the incident angle 2038 is 45 degrees, the refracted angle 3209 would be 50.6 degrees. FIG. 21 does not illustrate the small amount of light that is reflected about point 2036 as it is typically negligible. Refraction works in this manner until the incident angle 2038 is greater than the so-called critical angle $A_c$. For incident angles greater than the critical angle, the ray is reflected at the intersection point 2. The critical angle is calculated from equation (35).

$$A_c = \arcsin\left(\frac{N_2}{N_1}\right)$$  (35)

Using the typical index of refraction values $N_1$ and $N_2$ given above, the critical angle is 66.3 degrees. In FIG. 21, incident ray 2041 intersects a micro-prism surface at intersection point 2042 which has a surface normal 2043. This incident ray 2041 makes an incident angle 2044 with respect to the surface normal 2043. If the incident angle is 70 degrees, then by equation (35) the ray is totally reflected at surface point 2042 and has reflection angle 2045 equal to incident angle 2044 and the reflected ray 2046 is the result. Not shown in FIG. 21 is the continued path of reflected ray 2046 as it is subsequently refracted by the micro-prism surface.

Figure 22:
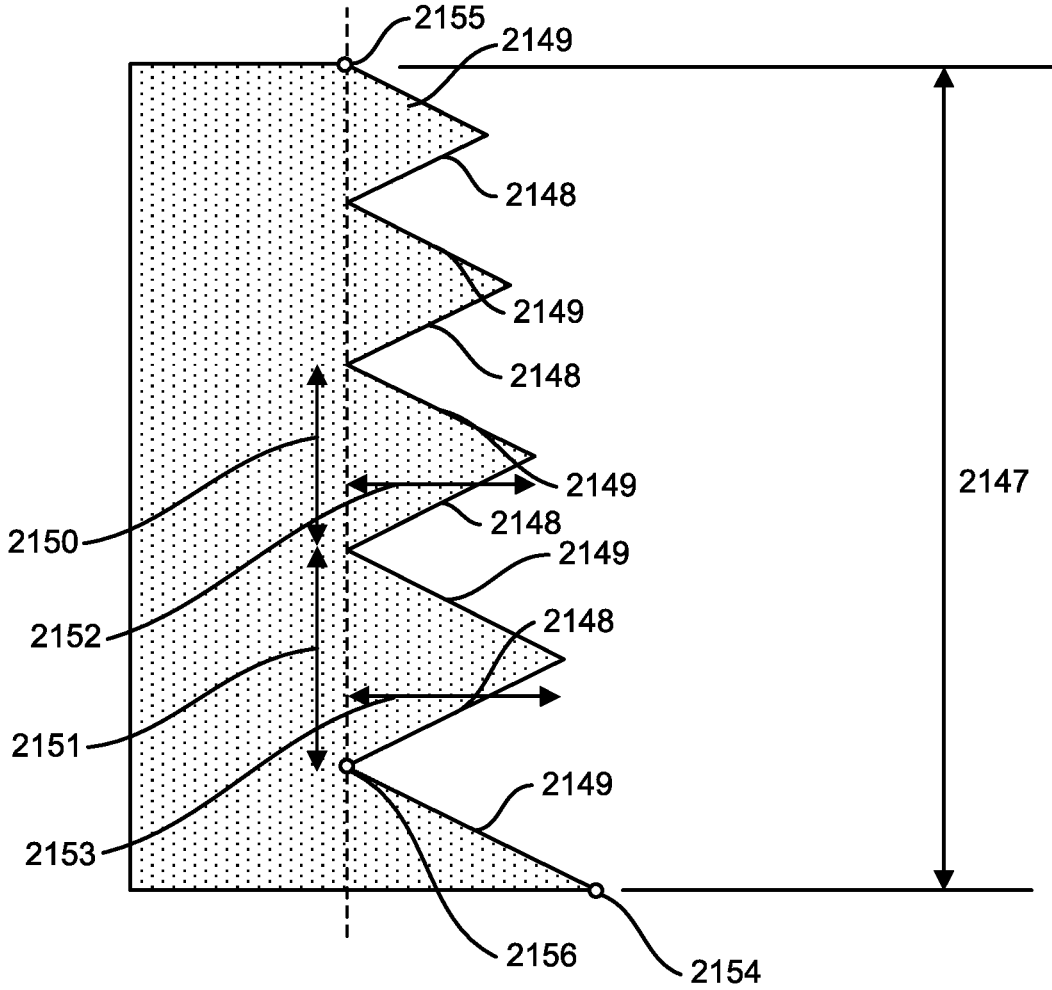
FIG. 22 shows an example structure of the micro-prism region.

In an example embodiment, the array of micro-prisms across the micro-prism region is not uniform. This non-uniformity is illustrated in FIG. 22. In FIG. 22, the total height 2147 is the distance from the end of the optical zone at the bottom of the figure to the start of the haptic at the top of the figure. Four and one-half micro-prisms are illustrated in FIG. 22. The micro-prisms decrease in size from the bottom of the figure to the top, while the location of the base of each micro-prism remains along a single X value shown as a dashed vertical line in the figure. As the size of the micro-prisms decreases, the slope of each of the lower and upper segments of a micro-prism remains constant.

All segment slopes 2148 are a constant value of 0.5 and all segment slopes 2049 are a constant value of −0.5. The decrease in size from the center of the lens (bottom of the figure) to the periphery (top of the figure) allows a decreasing lens thickness from the center of the lens to the haptic which is typical of IOLs. The height of the individual micro-prisms decreases in size from the bottom to the top following a geometric series. For example, the height 2150 of a micro-prism is equal to the height 2151 of the previous micro-prism times a scale factor a, where the scale factor is less than one. In the literature our scale factor a is also called the common ratio and is given the symbol r, but since we have already used the symbol r to refer to a fillet radius, we choose an alternate symbol a. Given the starting point $P_A$ 2154 at the edge of the optical zone and the ending point $P_B$ 2155 at the start of the haptic, the micro-prism slope s, and the common ration a, we calculate the geometry of the geometrically scaled micro-prisms using the following methods.

The start point P 2156 of the first complete micro-prism illustrated in FIG. 22 is given by equation (36).

$$P = \begin{bmatrix} Bx \\ A.y + s(B.x - A.x) \end{bmatrix}$$  (36)

where
  Coordinates of $P_A$ are denoted (A.x, A.y)
  Coordinates of $P_B$ are denoted (B.x, B.y)
  The base height $h_0$ 2151 of this first micro-prism is given by equation (37).

$$h_o = (P.y - A.y) \times 2 \times a$$  (37)

The series of micro-prism base heights is given by equation (38).

$$h_n = a h_{n-1} = a^n h_0$$  (38)

The sum of the individual base heights gives the total height H and is calculated using equation (39).

$$H = h_0 \sum_{n=0}^{N-1} a^n = h_0 \left( \frac{a^N - 1}{a - 1} \right) = B.y - P.y \quad (39)$$

The approximate number of individual micro-prisms N is calculated from equation (40).

$$N = \left\lceil \frac{\log\left( H \frac{a-1}{h_0} + 1 \right)}{\log(a)} \right\rceil \quad (40)$$

Given the integer number of individual micro-prisms N calculated in equation (12), we refine the initial base width $h_0$ so that we end up exactly at point $P_B$ 2155. This fine tuning of the initial base width is performed using equation (41).

$$h_0 = H \frac{a-1}{a^N - 1} \quad (41)$$

Consecutive micro-Prism peak $Peak_n$ and valley $Valley_n$ points for each micro-Prism n=0, . . . N−1, are calculated using equation (42).

$$Peak_n = Valley_{n-1} + \frac{h_{n-1}}{2} \begin{bmatrix} 1 \\ s \\ 1 \end{bmatrix} \quad (42)$$

$$Valley_n = Valley_{n-1} + \frac{h_{n-1}}{2} \begin{bmatrix} 0 \\ 1 \end{bmatrix}$$

$$h_n = a\, h_{n-1}$$

Figure 23:
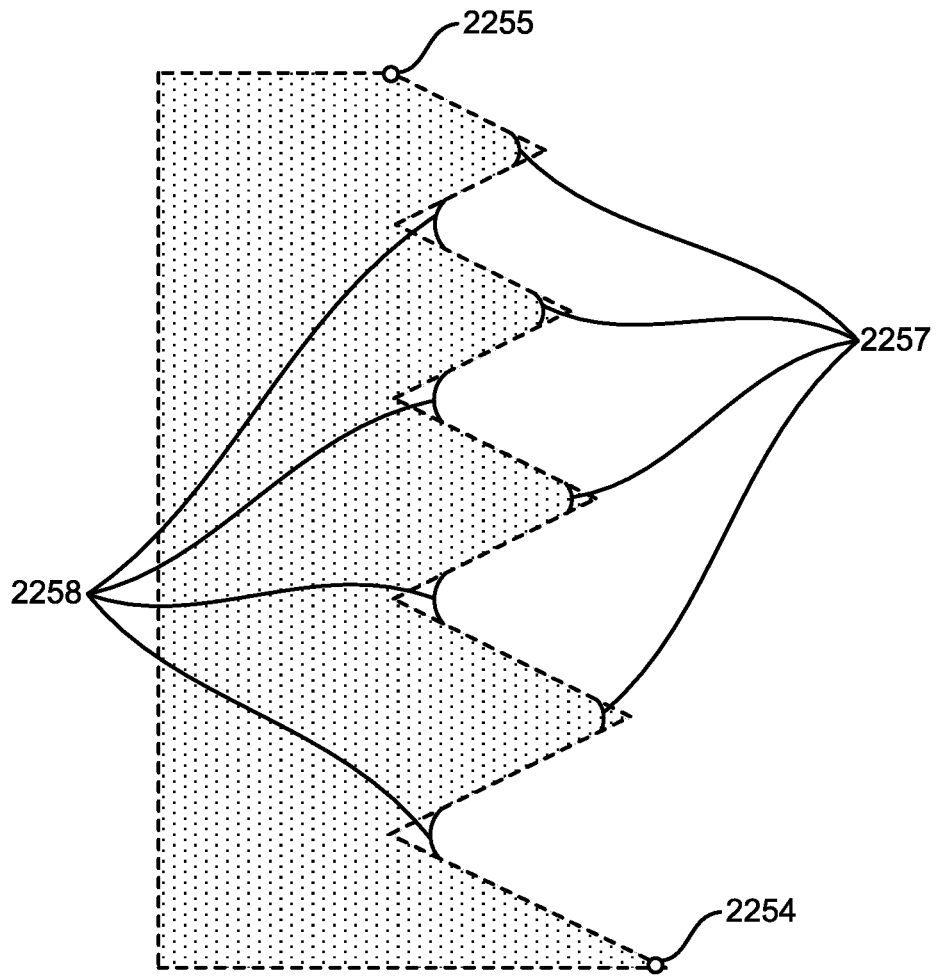
FIG. 23 shows the valley and peak fillets in the micro-prism region.

After these peak and valley vertex points are located, there is applied peak and valley fillets as illustrated in FIG. 23. These fillets are calculated using the methods described in conjunction with FIG. 18 and equations (29)-(31). For these fillets to respect proper sign conventions, the valley fillets (concave) will have positive radii and the peak fillets (convex) will have negative radii.

Figure 24:
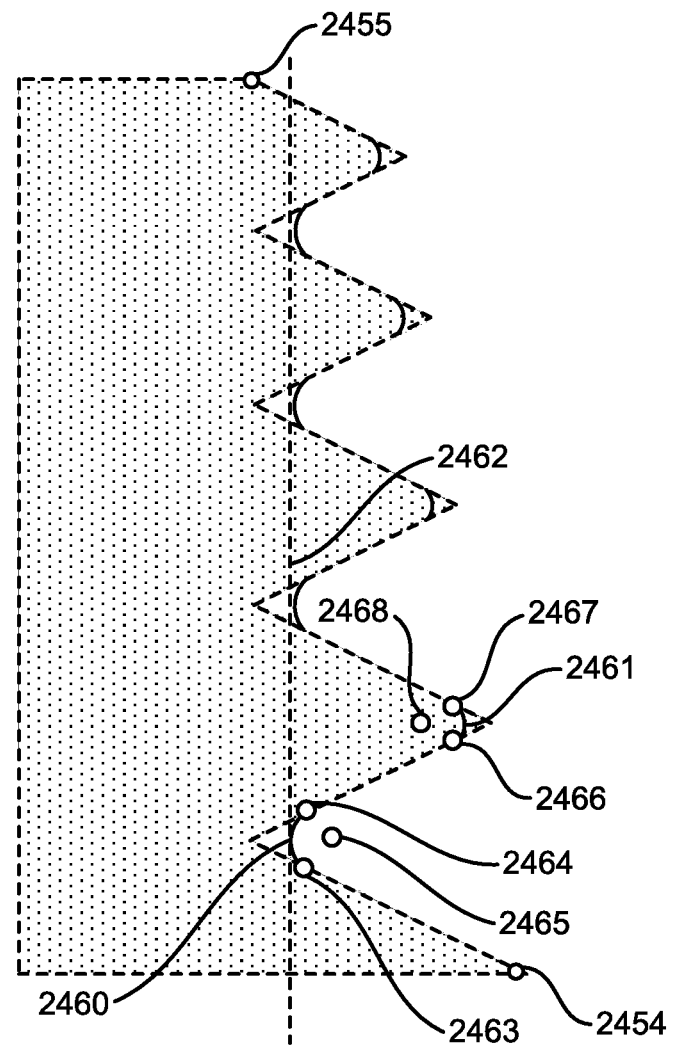
FIG. 24 shows an example configuration for a first valley fillet and a first peak fillet.

For example, the first valley fillet is shown in FIG. 24 as item 2460. The vertical dashed line 2462 in FIG. 24 is coincident with the vertex of each valley fillet and has the same x-coordinate value $X_V$. The center CV 2465 of each valley fillet has the same x-coordinate given by equation (43).

$$CV_X = X_V + r_V \quad (43)$$

In this equation $r_V$ is the radius of the valley fillet. The center CV of each valley fillet has its y-coordinate given by the corresponding $Valley_n$ points given by equation (42). The bounding points for the fillet circle are denoted P0 2463 and P1 2464 in FIG. 24. The coordinates for points P0 and P1 are given in equations (44).

$$P0_n = CV_n + r_V \frac{\begin{bmatrix} -s \\ -1 \end{bmatrix}}{\sqrt{1+s^2}} \quad (44)$$

-continued $$P1_n = CV_n + r_V \frac{\begin{bmatrix} -s \\ 1 \end{bmatrix}}{\sqrt{1+s^2}}$$

In these equations, the subscript n denotes the valley number. As shown in FIG. 24, the valley fillet circle radius $r_V$ is given a positive value.

For the peak fillets as illustrated in FIG. 24 item 2461, we first find the peak using equation (42), then find the peak fillet circle center CP using equation (45).

$$CP_n = Peak_n - \begin{bmatrix} r_P \sqrt{1 + \frac{1}{s^2}} \\ 0 \end{bmatrix} \quad (45)$$

In this equation $r_P$ is the radius of the peak fillet circle. Similar to the valley start and end points, the peak fillet circle start and end points P0 and P1, respectively, are calculated using equations (46).

$$P0_n = CP_n + r_P \frac{\begin{bmatrix} s \\ -1 \end{bmatrix}}{\sqrt{1+s^2}} \quad (46)$$

$$P1_n = CP_n + r_P \frac{\begin{bmatrix} s \\ 1 \end{bmatrix}}{\sqrt{1+s^2}}$$

FIG. 24 illustrates the peak fillet circle center, start point, and end point as items 2468, 2466, and 2467, respectively.

Figure 25:
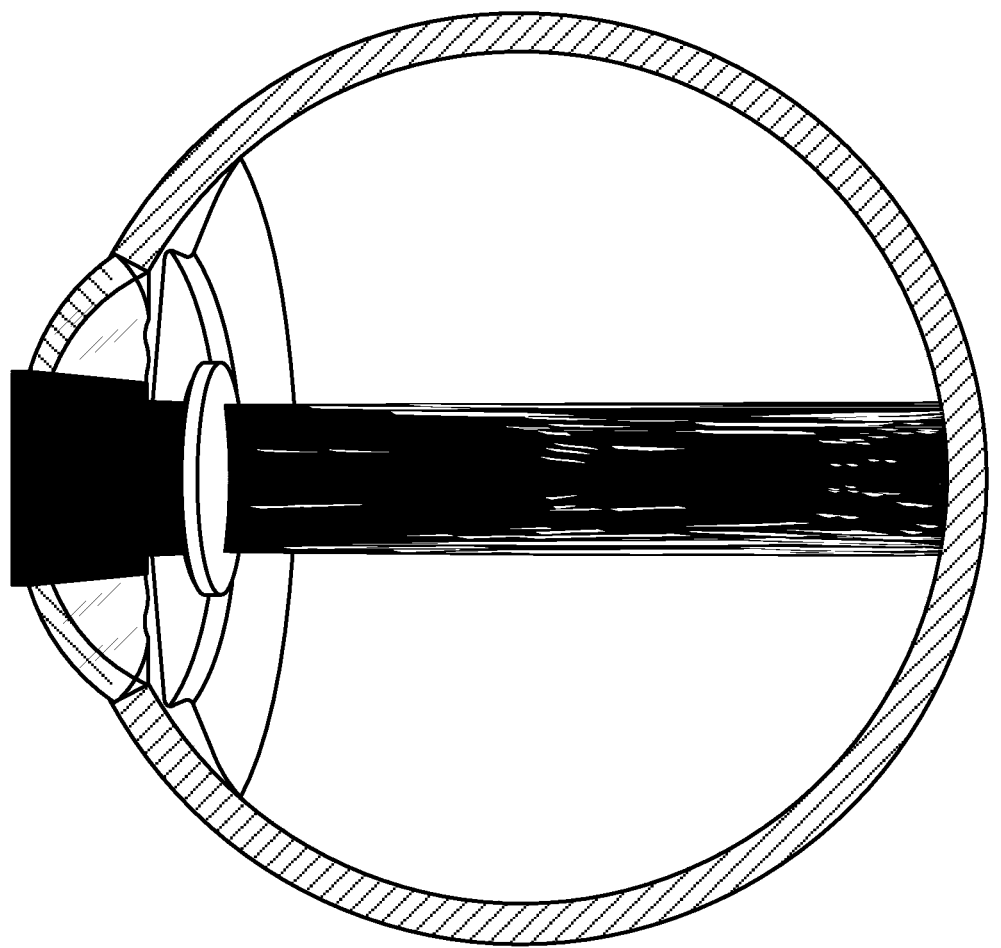
FIG. 25 shows the spreading of stray light in a ripple virtual aperture front surface and a smooth back surface IOL.
Figure 26:
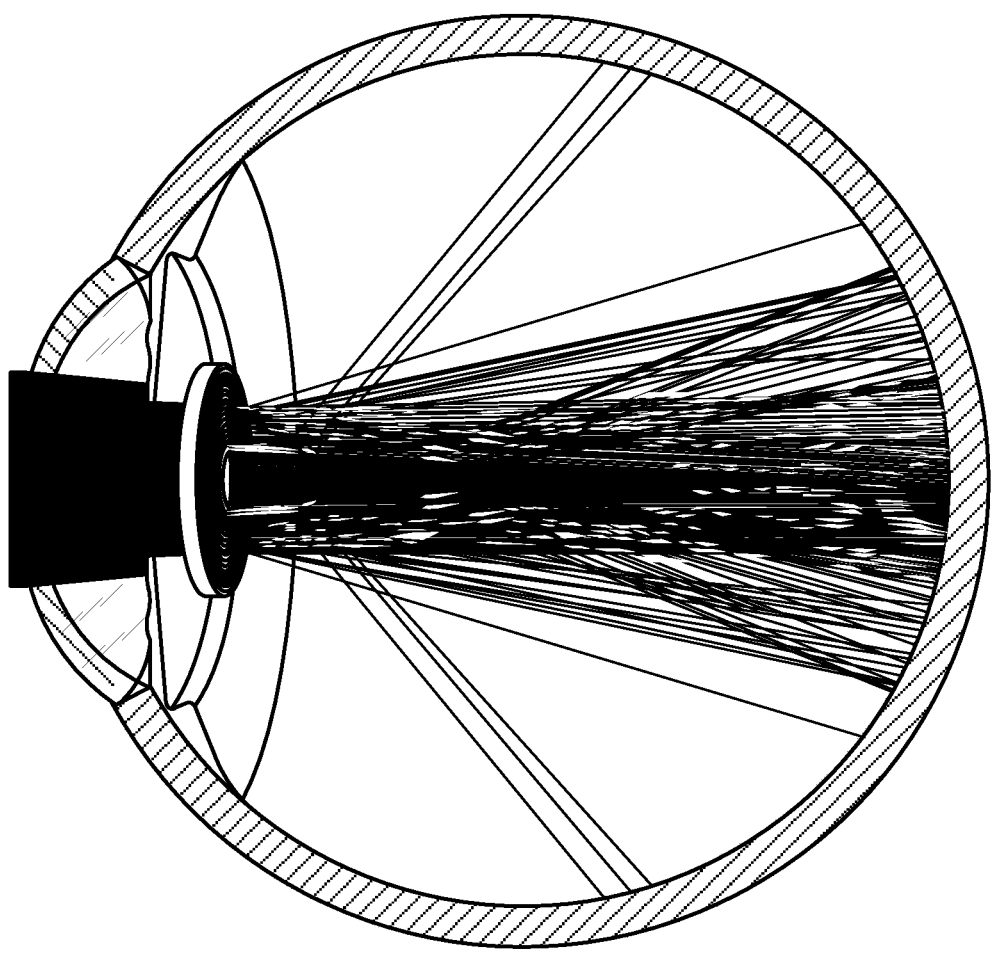
FIG. 26 shows the increased spreading of stray light in a ripple virtual aperture front surface and a micro-prism back surface IOL.

FIG. 25 illustrates how rays are distributed through a Z+ IOL with a front surface ripple zone and a back surface smooth zone. FIG. 26 illustrates the improved spreading of the light rays across the retina when the back surface is replaced with one incorporating the micro-prism region.

As an alternative to the circular fillets described above, one skilled in the art could use other transition methods such as Bezier curves.

In some applications it may be advantageous to use randomized fillet radii and/or micro-prism slope values.

Example Embodiment Values and Value Ranges

In example embodiments specific values are selected for the above micro-prism features. Additionally, these values could also be selected from reasonable ranges about the preferred values. These values and ranges are listed in the table below.

| Parameter | Value | Minimum | Maximum |
| --- | --- | --- | --- |
| Micro-prism region height | 2.25 mm | 1.5 mm | 2.75 mm |
| Valley fillet radius | 0.02 mm | (tool radius) | 0.06 mm |
| Peak fillet radius | 0.01 mm | 0.0 mm | 0.06 mm |
| Micro-prism slope | 0.5 | 0.25 | (critical angle) |
| Micro-prism to haptic fillet radius | 0.05 mm | (tool radius) | 0.06 mm |
| Micro-prism to optic zone fillet radius | 0.01 mm | 0.0 mm | 0.06 mm |

PCO (Posterior Capsule Opacification) Barrier

Posterior capsule opacification (PCO) is a complication that can occur after cataract surgery. To reduce the migration of cells into the virtual aperture or micro-prism regions, a sharp square edge can present at the haptic. In addition, the

23

Figure 27:
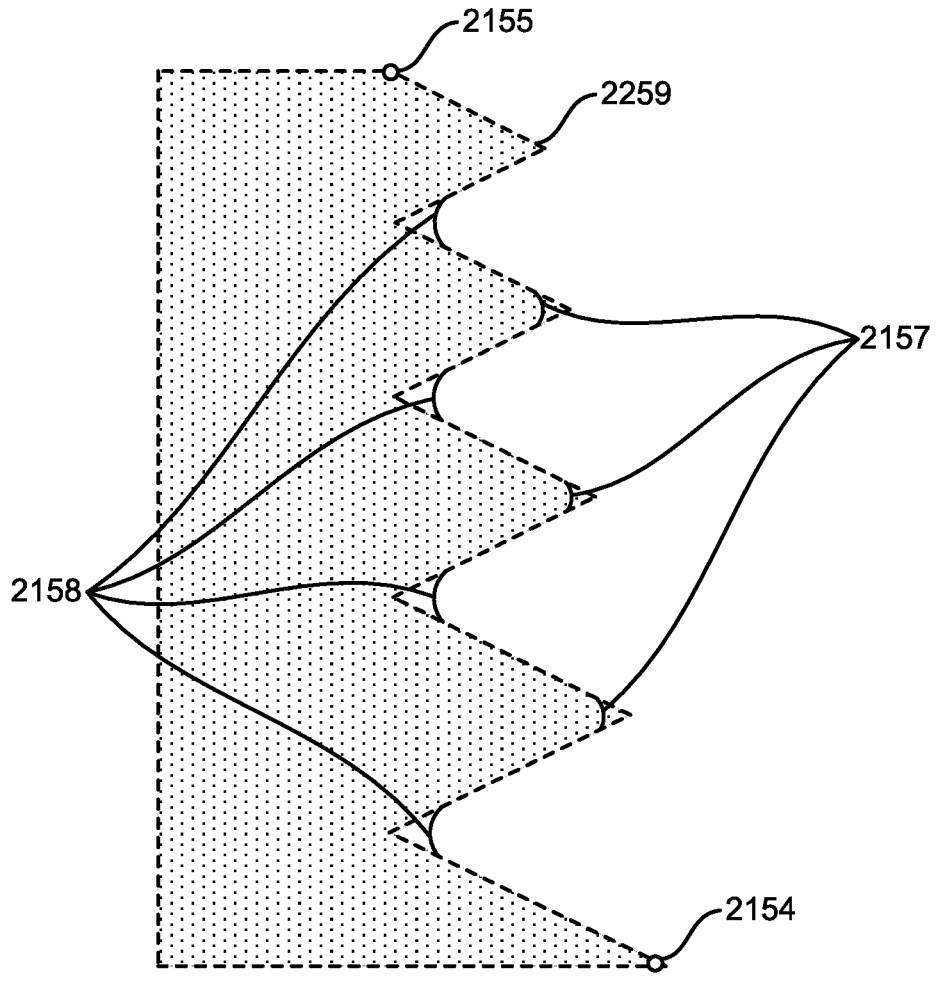
FIG. 27 shows a sharp last peak of a micro-prism.

24 last peak in the micro-prism region does not necessarily have a fillet on the peak. Such a sharp last peak is illustrated in FIG. 27 as peak 2559.

To use the concepts described above for the surface of the Z+ IOL the following is performed. First, the central optic of the IOL is specified. The diameter of the optic zone is around 1.5 mm and between (1.4 and 1.6 mm) in nonlimiting examples. Optical powers for this optic zone vary from −10 to 40 D in steps or 0.25 or 0.5 D. Cylinder powers for toric IOLs vary from 0.5 to 6.0 D in steps of 0.25 to 0.5 D.

The virtual aperture is then generated using the concepts described in previous disclosures. The width of the virtual aperture region is about 2.0 mm.

The width of the front surface transition regions is each set to around 0.15 mm. Dimensions for the back surface micro-prism region is described in the table above.

Once the front and back surfaces have been specified, individual profile samples are taken from the center of the IOL to the periphery to specify the points for the lathe cutting file.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

The invention claimed is:

1. An intraocular lens for providing an extended depth-of-field, said intraocular lens comprising:
    an optical zone comprising at least one anterior optical surface and at least one posterior optical surface;
    a first periphery region peripherally positioned relative to the optical zone, the first periphery region comprising a virtual aperture, the virtual aperture comprising an anterior virtual aperture surface and a posterior virtual aperture surface; and
    a second periphery region peripherally positioned relative to the first periphery region, the second periphery region comprising a haptic for positioning the intraocular lens within an eye, wherein the haptic comprises an outermost region of the intraocular lens;
    wherein a first plurality of light rays incident on the anterior optical surface pass through the optical zone to form an image on a retina when the intraocular lens is implanted in an eye; and at least one of:
    (a) a first surface contour on an anterior surface of the intraocular lens, the first surface contour comprising at least one annular region; and
    (b) a second surface contour on a posterior surface of the intraocular lens, the second surface contour comprising at least one annular region;
    wherein a second plurality of light rays incident on the anterior virtual aperture surface are dispersed widely downstream from the intraocular lens towards and across the retina, such that the image comprises the extended depth-of-field and further wherein said virtual aperture reduces monochromatic and chromatic aberrations in the image;
    wherein the second surface contour comprises a micro-prism array, and
    wherein the array of micro-prisms across the micro-prism region is not uniform.

2. The intraocular lens of claim 1, wherein the intraocular lens includes both the first surface contour and the second surface contour.

3. The intraocular lens of claim 1, wherein the first surface contour comprises at least one of a ripple and a micro-prism.

4. The intraocular lens of claim 1, wherein the second surface contour comprises at least one of a ripple and a micro-prism.

5. The intraocular lens of claim 1, wherein the first surface contour comprises a first annular region formed of at least one ripple and a second annular region formed of at least one micro-prism.

6. The intraocular lens of claim 1, wherein the second surface contour comprises a first annular region formed of at least one ripple and a second annular region formed of at least one micro-prism.

7. The intraocular lens of claim 1, wherein the first surface contour is located on the virtual aperture.

8. The intraocular lens of claim 1, wherein the second surface contour is located on the virtual aperture.

9. The intraocular lens of claim 1, wherein the first surface contour comprises at least one ripple.

10. The intraocular lens of claim 1, wherein the optical zone is separated from the virtual aperture by a first transition region.

11. The intraocular lens of claim 1, wherein the virtual aperture is separated from the haptic by a second transition region.

12. The intraocular lens of claim 1, wherein the first surface contour comprises a ripple on the virtual aperture and the second surface contour comprises a micro-prism on the virtual aperture.

13. The intraocular lens of claim 12, wherein the virtual aperture is separated from the haptic by a second transition region comprising a fillet.

14. The intraocular lens of claim 13, wherein the fillet has a curved contour.

15. The intraocular lens of claim 1, wherein the second surface contour includes a micro-prism peak.

16. The intraocular lens of claim 15, wherein the micro-prism peak provides a PCO barrier.

17. A method of treating an eye, comprising:
    implanting an ocular implant into the eye, the ocular implant comprising:
    an optical zone comprising at least one anterior optical surface and at least one posterior optical surface;

a first periphery region peripherally positioned relative to the optical zone, the first periphery region comprising a virtual aperture, the virtual aperture comprising an anterior virtual aperture surface and a posterior virtual aperture surface; and a second periphery region peripherally positioned relative to the first periphery region, the second periphery region comprising a haptic for positioning the intraocular lens within an eye, wherein the haptic comprises an outermost region of the intraocular lens;

wherein a first plurality of light rays incident on the anterior optical surface pass through the optical zone to form an image on a retina when the intraocular lens is implanted in the eye; and at least one of:

(a) a first surface contour on an anterior surface of the intraocular lens, the first surface contour comprising at least one annular region; and (b) a second surface contour on a posterior surface of the intraocular lens, the second surface contour comprising at least one annular region;

wherein a second plurality of light rays incident on the anterior virtual aperture surface are dispersed widely downstream from the intraocular lens towards and across the retina, such that the image comprises the extended depth-of-field and further wherein said virtual aperture reduces monochromatic and chromatic aberrations in the image;

wherein the second surface contour comprises a micro-prism array, and wherein the array of micro-prisms across the micro-prism region is not uniform.

* * * * *